United States Patent
McNeely et al.

(10) Patent No.: US 11,305,236 B2
(45) Date of Patent: *Apr. 19, 2022

(54) SURFACE TENSION DRIVEN FILTRATION

(71) Applicant: GattaCo Inc., Murrieta, CA (US)

(72) Inventors: Michael Ryan McNeely, Murrieta, CA (US); Mahmoud Zubaidi, Murrieta, CA (US)

(73) Assignee: GattaCo Inc., Murrieta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/013,032

(22) Filed: Sep. 4, 2020

(65) Prior Publication Data
US 2020/0398225 A1    Dec. 24, 2020

Related U.S. Application Data

(60) Continuation-in-part of application No. 16/513,518, filed on Jul. 16, 2019, now Pat. No. 10,870,085, (Continued)

(51) Int. Cl.
*B01D 63/08* (2006.01)
*G01N 33/49* (2006.01)

(52) U.S. Cl.
CPC ......... *B01D 63/087* (2013.01); *G01N 33/491* (2013.01)

(58) Field of Classification Search
CPC .... B01D 61/18; B01D 63/005; B01D 63/028; B01D 63/087; G01N 33/491
See application file for complete search history.

(56) References Cited

U.S. PATENT DOCUMENTS

| 5,135,716 A | 8/1992 | Thakore |
| 6,296,020 B1 | 10/2001 | Mcneely et al. |

(Continued)

FOREIGN PATENT DOCUMENTS

| AU | 2015275031 | 1/2017 |
| AU | 2015275031 | 10/2019 |

(Continued)

OTHER PUBLICATIONS

"International Application Serial No. PCT US2015 034608, International Search Report dated Sep. 2, 2015", 2 pgs.

(Continued)

*Primary Examiner* — Bradley R Spies
(74) *Attorney, Agent, or Firm* — Schwegman Lundberg & Woessner, P.A.

(57) ABSTRACT

Disclosed is a device for extracting a filtrate from a liquid sample that includes one or more filtration membranes and, in physical contact with a portion of the downstream surface(s) of the filtration membrane(s), a soluble matrix possessing a capillary drawing force sufficient to draw filtrate through the at least one filtration membrane and into the soluble matrix, causing the soluble matrix to at least partially dissolve or disintegrate in the filtrate, whereby the filtrate is released. Various configurations, including device configurations having two filtration membranes with a soluble matrix in between or having a tubular filtration membrane at least partially surrounding or surrounded by a soluble matrix are described.

21 Claims, 10 Drawing Sheets

Related U.S. Application Data which is a division of application No. 15/312,311, filed as application No. PCT/US2015/034608 on Jul. 7, 2015, now Pat. No. 10,532,325.

(60) Provisional application No. 62/895,904, filed on Sep. 4, 2019, provisional application No. 62/011,661, filed on Jun. 13, 2014.

(56) References Cited

U.S. PATENT DOCUMENTS

| | | | |
|---|---|---|---|
| 6,811,842 | B1 | 11/2004 | Ehrnsperger et al. |
| 8,747,669 | B1 | 6/2014 | Bonner et al. |
| 10,532,325 | B2 | 1/2020 | Mcneely |
| 10,870,085 | B2 | 12/2020 | McNeely |
| 2004/0004037 | A1 | 1/2004 | Herron |
| 2004/0035792 | A1 | 2/2004 | Rauch et al. |
| 2006/0228259 | A1* | 10/2006 | Samsoondar .... A61B 5/150755 422/82.05 |
| 2007/0031283 | A1* | 2/2007 | Davis ............... A61B 5/150221 422/400 |
| 2007/0269893 | A1 | 11/2007 | Blankenstein et al. |
| 2011/0135546 | A1 | 6/2011 | Kurowski et al. |
| 2012/0080147 | A1 | 4/2012 | Offeman et al. |
| 2012/0118392 | A1 | 5/2012 | Blankenstein et al. |
| 2013/0112612 | A1 | 5/2013 | Blankenstein et al. |
| 2013/0142708 | A1 | 6/2013 | Battrell et al. |
| 2014/0295415 | A1* | 10/2014 | Rolland .................... B01L 7/52 435/6.1 |
| 2015/0111194 | A1* | 4/2015 | Rempfer .............. B01J 20/3291 435/2 |
| 2015/0226732 | A1* | 8/2015 | De Theije ........ G01N 33/54326 436/500 |
| 2015/0367288 | A1 | 12/2015 | Haynes et al. |
| 2016/0339159 | A1* | 11/2016 | Nosaka .................. B01D 63/02 |
| 2017/0087517 | A1 | 3/2017 | Mcneely |
| 2017/0354361 | A1* | 12/2017 | Tan .................. A61B 5/150343 |
| 2019/0153524 | A1* | 5/2019 | Hayden ................ C12Q 1/6853 |
| 2019/0336916 | A1 | 11/2019 | Mcneely |
| 2021/0229041 | A1 | 7/2021 | Mcneely |

FOREIGN PATENT DOCUMENTS

| | | | | |
|---|---|---|---|---|
| CA | 2949863 | | 12/2015 | |
| CA | 2949863 | | 10/2017 | |
| CA | 3029274 | A1 * | 3/2018 | ........... C12Q 1/6853 |
| CN | 1262629 | | 8/2000 | |
| CN | 106573201 | | 4/2017 | |
| CN | 106573201 | | 5/2020 | |
| EP | 3154666 | | 4/2017 | |
| EP | 3154666 | | 12/2020 | |
| WO | 2012178187 | | 12/2012 | |
| WO | 2015044454 | | 4/2015 | |
| WO | 2015191406 | | 12/2015 | |

OTHER PUBLICATIONS

"International Application Serial No. PCT US2015 034608, Written Opinion dated Sep. 2, 2015", 5 pgs.
"International Application Serial No. PCT US2015 034608, International Preliminary Report on Patentability dated Dec. 22, 2016", 7 pgs.
"U.S. Appl. No. 15/312,311, Preliminary Amendment filed Nov. 21, 2016", 2 pgs.
"U.S. Appl. No. 15/312,311, Restriction Requirement dated Aug. 28, 2018", 7 pgs.
"U.S. Appl. No. 15/312,311, Response filed Oct. 18, 2018 to Restriction Requirement dated Aug. 28, 2018", 1 pg.
"U.S. Appl. No. 15/312,311, Non Final Office Action dated Dec. 3, 2018", 10 pgs.
"U.S. Appl. No. 15/312,311, Response filed Feb. 28, 2019 to Non Final Office Action dated Dec. 3, 2018", 9 pgs.
"U.S. Appl. No. 15/312,311, Notice of Non-Compliant Amendment dated Mar. 7, 2019", 1 pg.
"U.S. Appl. No. 15/312,311, Response filed Apr. 23, 2019 to Notice of Non-Compliant Amendment dated Mar. 7, 2019", 9 pgs.
"U.S. Appl. No. 15/312,311, Notice of Non-Compliant Amendment dated May 13, 2019", 2 pgs.
"U.S. Appl. No. 15/312,311, Response filed May 14, 2019 to Notice of Non-Compliant Amendment dated May 13, 2019", 11 pgs.
"U.S. Appl. No. 15/312,311, Notice of Allowance dated Jul. 1, 2019", 7 pgs.
"Brazilian Application Serial No. 112016028752-5, Office Action dated Jan. 27, 2020", with English translation, 6 pages.
"Indian Application Serial No. 201627041196, First Examination Report dated Jan. 7, 2020", with English translation, 6 pages.
"Canadian Application Serial No. 2949863, Voluntary Amendment filed Nov. 21, 2016", 4 pgs.
"Canadian Application Serial No. 2949863, Office Action dated Dec. 12, 2016", 6 pgs.
"Canadian Application Serial No. 2949863, Office Action dated Jun. 2, 2017", 6 pgs.
"Canadian Application Serial No. 2949863, Response filed Aug. 17, 2017 to Office Action dated Jun. 2, 2017", 12 pgs.
"Canadian Application Serial No. 2949863, Response filed Feb. 6, 2017 to Office Action dated Dec. 12, 2016", 47 pgs.
"Australian Application Serial No. 2015275031, First Examiner Report dated Mar. 26, 2019", 3 pgs.
"Australian Application Serial No. 2015275031, Response filed Aug. 16, 2019 to First Examiner Report dated Mar. 26, 2019", 2 pgs.
"European Application Serial No. 15806956.7, Communication Pursuant to Article 94(3) EPC dated Sep. 11, 2019", 5 pgs.
"European Application Serial No. 15806956.7, Extended European Search Report dated Jan. 19, 2018", 8 pgs.
"Malaysian Application Serial No. 2016704540, Substantive Examination Adverse Report dated Mar. 22, 2020", 3 pgs.
"Chinese Application Serial No. 201580042907.7, Office Action dated Dec. 19, 2018", with English translation, 18 pages.
"Chinese Application Serial No. 201580042907.7, Response filed Apr. 30, 2019 to Office Action dated Dec. 19, 2018", with English claims, 8 pages.
"Chinese Application Serial No. 201580042907.7, Office Action dated Aug. 12, 2019", with English translation, 13 pages.
"Chinese Application Serial No. 201580042907.7, Response filed Sep. 30, 2019 to Office Action dated Aug. 12, 2019", with English claims, 5 pages.
"Brazilian Application Serial No. 112016028752-5, Response filed May 1, 2020 to Office Action dated Jan. 27, 2020", with English claims, 11 pages.
"European Application Serial No. 15806956.7, Response to Communication pursuant to Rules 161(1) and 162 EPC filed Aug. 9, 2017", 13.
"European Application Serial No. 15806956.7, Response filed Jan. 9, 2020 to Communication Pursuant to Article 94(3) EPC dated Sep. 11, 2019", 9 pgs.
"European Application Serial No. 15806956.7, Response filed Jul. 19, 2018 to Extended European Search Report dated Jan. 19, 2018", 10 pgs.
"Malaysian Application Serial No. 2016704540, Response filed May 20, 2020 to Substantive Examination Adverse Report dated Mar. 22, 2020", 52 pgs.
"U.S. Appl. No. 16/513,518, Notice of Allowance dated Aug. 10, 2020", 9 pgs.
"Mexican Application Serial No. MX a 2016 016536, Office Action dated Jul. 16, 2020", with English Translation, 8 pages.
"U.S. Appl. No. 17/126,322, Preliminary Amendment filed Apr. 19, 2021", 7 pages.

* cited by examiner

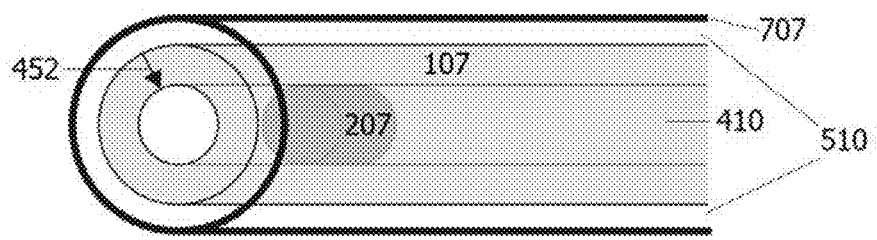
FIG. 17
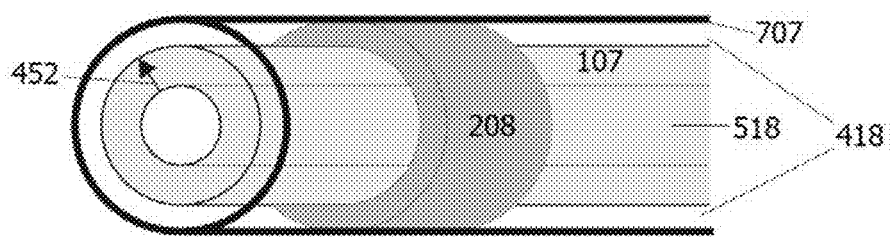
FIG. 18
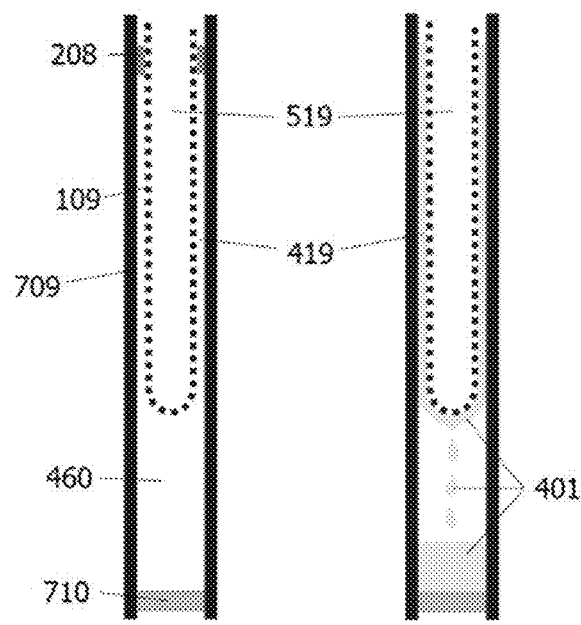
FIG. 19A   FIG. 19B

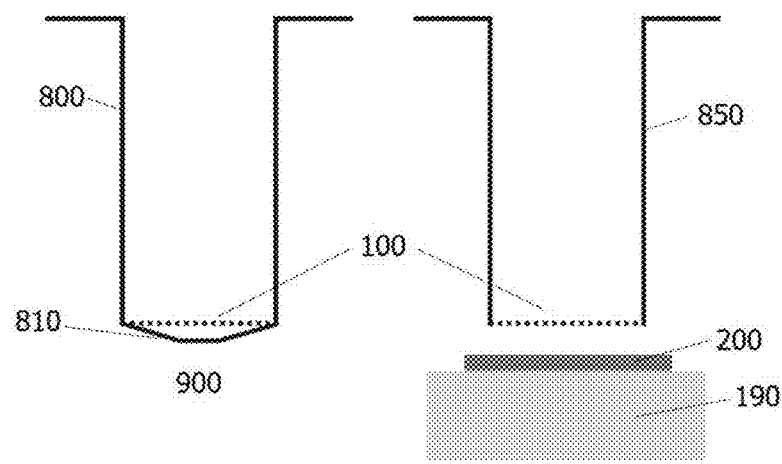
*FIGS. 22A*  *FIG. 22B*

SURFACE TENSION DRIVEN FILTRATION

CROSS-REFERENCE TO RELATED APPLICATIONS

This application claims priority to and the benefit of U.S. Provisional Patent Application No. 62/895,904, filed on Sep. 4, 2019. This application further is a continuation-in-part of U.S. patent application Ser. No. 16/513,518, filed on Jul. 16, 2019, which is a divisional of U.S. patent application Ser. No. 15/312,311, filed on Nov. 18, 2016, now U.S. Pat. No. 10,532,325, which is a § 371 national-stage application of International Patent Application No. PCT/US2015/034608, filed on Jun. 7, 2015, which claims benefit of U.S. Provisional Application No. 62/011,661, filed on Jun. 13, 2014. The disclosures of all priority application are incorporated herein by reference in their entireties.

TECHNICAL FIELD

This disclosure relates to methods and devices for reducing the pressure required to pass liquid through a filter or filters for the first time, particularly in relation to use in sample processing for medical diagnostic applications for the separation or fractionation of the input liquid sample into aqueous and particulate components.

BACKGROUND

Many filtration systems experience a transient spike of liquid flow pressure as liquid is passing through the filtration system for the first time. However, once liquid has passed through a filter, a steady state pressure is reached which can be significantly lower than the initial pressure spike. In large, industrial filtration systems, this transient pressure spike is usually of little concern, because the whole system is designed to withstand this spike. However, in low cost, handheld, disposable systems, managing this pressure requirement can be very difficult, expensive, or impossible.

This pressure spike is caused by the capillarity of the filter itself. If the filter material is hydrophobic, aqueous liquid will not want to enter the filter and the increased pressure is required to force the liquid in. If the filter material is hydrophilic, aqueous liquid will not want to leave the filter, but is tightly held within the pore structure of the filter, and the pressure transient is needed to push the liquid through, or out, of the filter (breakthrough pressure). However, once liquid is flowing through the filter, the capillarity of the filter ceases to exist, and flow is governed by a different set of conditions that does not include the hydrophilicity or hydrophobicity of the filter material, but rather its pore size, percent porosity, liquid viscosity, flow rates, and any relevant downstream flow conditions. This is the steady state condition.

This disclosure will discuss hydrophilic systems, or systems where the filter is made of a hydrophilic material, or where the filter or critical surfaces of the filter can be rendered hydrophilic.

The term "capillarity" refers to capillary forces that exist at a liquid/gas interface, or liquid/air interface, where surface tension, or interface tension, exists between the liquid and the air. Capillarity is dependent on the dimensions of the system, such as the pore size of the filter, the type of liquid (e.g., whether it is aqueous or organic, its salt content, etc.), and the surface properties of the flow channel, such as whether it is hydrophobic or hydrophilic, including the degree of hydrophobicity or hydrophilicity (contact angle). Once liquid has been pushed through a filter, the liquid/air interface is no longer present in the filter, which is why the capillary forces or capillarity cease to exist within the filter.

In contrast to pressure transients experienced by filtration systems, another system, referred to as a lateral flow system, exists where no pressure transient takes place and, in fact, no externally applied pressure is required to pass liquid through filters or membranes. In a lateral flow system, capillary forces completely control the flow of liquid through the system. Different filters, including filtration membranes, are layered one on top of each other, and liquid passes from one filter to the next due to the increased capillarity of each successive filter. A filtration membrane that is often used in such systems is the PALL Vivid™ Plasma Separation Membrane that is capable of separating plasma from whole blood. Normally, such filtration, due to the small pore size, would require substantial pressure to force the plasma or serum to exit the filter. Such high pressure often causes hemolysis or breaking of red blood cells in the whole blood, which reduces the quality of the filtrate. Instead, according to operational instructions of the filter itself, all that is required to extract the plasma through the filter is to place the filter on another filter or membrane of higher capillarity; then flow proceeds automatically.

However, what if it is desired to remove the plasma from the filter, or from a successive filter? This is difficult to do using traditional technologies. Instead, if it is desired to separate plasma from whole blood in a non-filtration filter system, a centrifuge is usually used.

Many new medical diagnostic systems use microfluidic technologies to control liquid flow, process liquid samples, and analyze their content. Microfluidics involves the processing and movement of liquid through small channels, such as channels between 0.1 and 1000 µm in diameter. Liquid flow is controlled by capillary forces, positive pressure pumps, suction, or electric forces. These include the processing and analysis of whole blood. In some of these systems attempts are made to separate plasma from whole blood. However, whenever the microfluidic flow channels become very small, such as less than 1 and 5 µm in diameter, such as what may be needed to separate plasma from whole blood, the system quickly becomes impractical to commercialize due to the very expensive manufacturing methods that are required to produce products reliably with such small dimensions, or due to the extremely low flow rates that are generated, or very high pumping pressures that may be required if the system is driven by positive pressure, or because of the difficulty in sealing such a system due to high pressures or high probability of blocking small flow channels during the sealing process, or due to some other related complication.

The use of a filter to separate plasma from whole blood has several advantages over the use of microchannels or a network of microchannels for separation. These advantages include the fact that filters for this purpose are already commercially available in large quantities, are relatively inexpensive, robust, durable, and easy to use. Also, their quality and manufacture can be controlled, tested and performed 'off-line' of the quality and control and manufacture of a complete diagnostic system. They do not represent a limiting factor in the production of a diagnostic device, which is in strong contrast to the use of microchannels as a means of size-exclusion-based filtration.

It is highly desirable and beneficial for a system to be developed that has the advantages of filter-based filtration, but does not require the filtrate to be retained and processed within a downstream filter system, and does not require the use of buffer, diluent, solvent, or pressure in order to cause the filtrate to be passed through the filter and be available for collection. It is also desirable for this method of filtration, when used for medical diagnostics, to be able to interface directly with enclosed microfluidic-based diagnostics, or to be collectable and used in some macro-diagnostic system, or even reintroduced to a filter-based systems after additional processing on the filtrate has taken place, such as metering or measuring the amount of filtrate that is present before it is passed downstream.

The most common method of separating plasma from whole blood is not filtration, but centrifugation. While centrifugation is often used to force liquids through filters, it is, in and of itself, a method of separation or fractionation, by means of density gradients rather than size.

In biological sample processing, centrifugation is commonly used to separate or fractionate blood into various layers such as red blood cells, white blood cells, and plasma. Centrifugation of blood is ubiquitous in the medical in-vitro diagnostics field, where blood is routinely drawn from a vein in the arm and passed into evacuated collection tubes. These collection tubes are centrifuge tubes and usually contain a cocktail of reagents to preserve and protect various components of the blood until they have been centrifuged and the fraction of interest, most often plasma, is removed from the tube and loaded into an analyzer.

Some blood analyzers are automated and make use of test-tube-type sample holders, similar to the centrifuge tubes. Another platform common in automated analysis are microplates formed of a number of small wells in column and row grid-like patterns. Some analyzers use functionalized glass, polymer, or magnetic beads to facilitate the analysis of interest. Analysis may be done on cellular fractions, such as circulating tumor cells, stem cells, bacteria, or genomic DNA located in white blood cells. Analysis of the plasma fraction may be done to investigate the presence of cell-free DNA, viral RNA, proteins, hormones, lipids, enzymes, or other components. Often the fraction of interest, or component within a fraction, may undergo a concentration step, to remove background or excess liquids so the target of interest can be more effectively interrogated.

SUMMARY

As has been discussed, capillary forces can be used to draw plasma, or any aqueous liquid, out of a small-pore hydrophilic filter, provided these capillary forces are greater than the capillarity of the filter itself. Once drawn out of the filter, the capillarity associated with this filter ceases to exist due to the removal of a liquid/air interface at or within the filter, or at the downstream junction of the filter and subsequent liquid flow system. The ability of these capillary forces to draw liquid out of a filter can be used to reduce or eliminate a pressure spike transient often associated with passing liquid through a small-pore filter for the first time. This disclosure details methods, processes, devices, and systems for drawing liquid out of a small-pore filter, or out of small-dimensioned microfluidic channels, by using a micro- or nano-particulate salt, sugar, protein, or other material that is soluble in the filter filtrate or microchannel system liquid. Initially, due to its particulate size and pore structure, which pore structure could be generated by the spaces in between individual granules or particles, which particles or granules may or may not be porous themselves, and due to the chemical composition of the granules or particles, including due to its hygroscopicity and ability to generate osmotic forces, this micro- or nano-particulate soluble material, or soluble matrix, possesses a higher capillarity, or higher liquid drawing force than the initial filter or microchannel with which it is in physical contact, so that the liquid passes out of its present position within the initial filter or microchannel and into the soluble matrix component. The soluble matrix is held in a flow channel or housing or system in physical contact with the initial filter or microchannel, but the geometry of said flow channel, housing, or system is of a much larger dimension than the pores of the initial filter or diameter of the microchannel. Over the course of seconds to minutes this soluble matrix dissolves in the liquid that has filled its pores, and the liquid now resides outside of the initial filter or microchannel, in a system of larger geometry where capillary forces, if they still exist, are much more manageable or lower than they were while the liquid was within the initial filter or microchannel.

In this manner, by using a soluble matrix with high initial capillarity, liquid within the initial filter or microchannel can be drawn out of the initial filter or microchannel by capillary forces without the need for any additional pressure or force. Stated in another way, a soluble matrix can be used to produce a material of temporary high capillarity, useful for drawing liquid out of a filter or microfluidic channel, which high capillarity becomes lower as the soluble matrix dissolves.

Another way to describe the use of this soluble matrix is that it acts as a capillary pressure re-set mechanism, or material, such that the capillary forces holding or retaining liquid at one point are overcome and re-set to the capillary forces that are defined by the geometry, material, and liquid type under a new set of conditions, which reset capillary forces are generally much lower than those of the system preceding it.

What is also useful about this design is that, by the strategic placement of the soluble matrix, and the strategic placement of a venting duct, the volume of filtrate that is in initial contact with the soluble matrix and that dissolves in it can be excluded from the volume of filtrate that is collected or moved downstream for further processing. In this manner, any negative or deleterious or interfering effect the soluble matrix may have in downstream processing of the filtrate can be reduced or completely eliminated.

Furthermore, the current disclosure also describes use of hydrophilic filters for not for just one surface, where the soluble matrix is bounded between a filter and a solid support, but also for two surfaces, where the soluble matrix is bound between two porous filters, which are also saturated with liquid and supply liquid to an advancing liquid column or meniscus. Such a geometry and application, to the authors' knowledge, has not been mathematically modeled, at least from a capillary force perspective. While it is not our intent to model this geometry, it is our intent to describe the applications, benefits and devices that can be derived from such a structure.

These structures are often planar in geometry, but may also be tubular, cylindrical, or cone-shaped, and can be modified to fit in tubes, as are often used in biological sample processing. Tubes are common in the workflow of traditional automated blood collection and testing platforms. Tubes are often used to separate particles, or cells, from plasma or other liquids. The structures under discussion may also be a component of a microplate format, and may, together with filters to separate fractions of a sample, be used together with beads of various kinds to capture and facilitate the collection, concentration, positive or negative enrichment, and/or detection of components within a fraction.

The structures for liquid separation may also be integrated into electrowetting liquid manipulation devices which enable retrieval of liquids from filters as an alternative to passive capillary forces.

The filtration structure may be also integrated into wearables or body attachable liquid collection and testing devices, and/or integrated with biosensors for complete sample-to-answer diagnostic testing.

The liquid separation, filtration or purification device may be functionalized with reagents to stabilize the samples, capture specific analytes for positive depletion, or negative depletion, for the purpose of detection and analysis of the analyte. The filtration structure may also be chemically or physically treated to reduce or eliminate non-specific binding of analytes of interest, for example by adding blocking chemistries to minimize non-specific binding sites, or salts to alter the charge of surfaces to modify charge-based binding effects.

In one aspect, a device for extracting a filtrate from a liquid sample is provided. The device includes at least one filtration membrane, and a soluble matrix in physical contact with at least a portion of a downstream surface of the at least one filtration membrane, the soluble matrix possessing a capillary drawing force sufficient to draw filtrate through the at least one filtration membrane and into the soluble matrix, causing the soluble matrix to at least partially dissolve or disintegrate in the filtrate, whereby the filtrate is released. The filtration membrane may be a plasma separation membrane. In some embodiments, the plasma separation membrane is treated to improve filtering performance for a specific biomarker, e.g., an antibody, antigen or nucleic acid component of or for a coronavirus. The device may include a base material, support membrane, or housing to hold the soluble matrix in contact with the at least one filtration membrane.

In some embodiments, the device includes two filtration membranes arranged substantially in parallel and facing each other with their downstream surfaces, holding the soluble matrix in between. The separation distance between the two filtration membranes is sufficiently small to cause the filtrate to wick along the downstream surfaces of the two filtration membranes upon at least partial dissolution or disintegration of the soluble matrix. The device may further include a housing containing the two filtration membranes and the soluble matrix therebetween and defining an inlet in fluid communication with upstream surfaces of the two filtration membranes and an outlet in fluid communication with downstream surfaces of the two filtration membranes and with the soluble matrix.

In some embodiments, the device includes multiple filtration membranes and soluble matrixes in an alternating sequence, wherein each downstream filtration membrane is in physical contact with a downstream surface of a preceding one of the soluble matrixes in the sequence, and wherein each of the downstream soluble matrixes is in physical contact with a preceding one of the filtration membranes in the sequence and possesses a capillary drawing force sufficient to draw filtrate through the preceding one of the filtration membranes and into the soluble matrix. The device may further include a housing containing the alternating sequence of filtration membranes and soluble matrixes and defining an inlet in fluid communication with an upstream surface of the first filtration membrane and outlets each in fluid communication with a downstream surface of one of the filtration membranes. Filter properties of the filtration membranes differ along the sequence, whereby the liquid sample is fractionated into a retentate fraction, one or more filtered retentate fractions, and a final filtrate fraction. Successive soluble matrixes in the sequence, one being in physical contact with an upstream surface of one of the downstream filtration membranes and another one being in physical contact with a downstream surface of that downstream filtration membrane, may be spaced apart along that downstream filtration membrane.

In some embodiments, the device includes a tubular filtration membrane. The soluble matrix may be placed inside the tubular filtration membrane in physical contact with an interior surface of the tubular filtration membrane, an inner diameter of the tubular filtration membrane being sufficiently small to cause the filtrate to wick along the cylindrical filtration membrane in a longitudinal direction upon at least partial dissolution or disintegration of the soluble matrix. A housing containing the tubular filtration membrane and the soluble matrix may define an inlet in fluid communication with an exterior surface of the tubular filtration membrane and an outlet in fluid communication with a center lumen of the tubular filtration membrane and with the soluble matrix. Alternatively, the soluble matrix may be placed at least partially surrounding the tubular filtration membrane in physical contact with an exterior surface of the cylindrical filtration membrane, and a tubular housing containing the filtration membrane and the soluble matrix may define an inlet in fluid communication with a center lumen of the tubular filtration membrane and with the soluble matrix, wherein a separation distance between an interior surface of the tubular housing and the exterior surface of the tubular filtration membrane is sufficiently small to cause the filtrate to wick along the tubular filtration membrane in a longitudinal direction upon dissolution or disintegration of the soluble matrix. In some embodiments, the device includes multiple nested tubular membranes with one or more soluble matrixes therebetween. In some embodiments, the soluble matrix lines an exterior surface of the tubular filtration membrane, and a housing of the device contains the lined tubular filtration membrane and a filtrate absorbing material filling a space between the lined tubular filtration membrane and the housing.

In some embodiments, the filtration membrane is conical in shape and supported by a conical sponge structure, and the soluble matrix is placed between the conical sponge structure and the conical filtration membrane. This device may include a tubular housing with a septum on which the conical sponge structure rests.

The foregoing summary is intended to introduce various concepts and example embodiments of the disclosed subject matter, but is neither exhaustive in the embodiments it mentions, nor intended to limit the scope of the claimed subject matter.

BRIEF DESCRIPTION OF THE DRAWINGS

The following drawings illustrate exemplary embodiments. There are, in fact, many possible liquids that may be processed, many possible filter or microchannel configurations, housings, flow systems, entrance and exit point designs, flow patterns, soluble matrix placements, dimensions and geometries, and liquid flow driving forces possible in various embodiments. The following examples only serve to illustrate principles discussed in this disclosure, and are not meant to be limiting in any way in converting the principles discussed in this disclosure into physical form, and are not necessarily to scale as may be used in a physical system. Like reference numerals refer to like parts in different views or embodiments.

FIG. 17 illustrates a tubular or cylindrical separation system with soluble matrix in the core of a tubular filter to facilitate separation and flow of filtrate from the outside to the inside of the tubular filter, according to an embodiment.

FIG. 18 illustrates a tubular or cylindrical separation system with soluble matrix between a cylindrical filter and filter housing to facilitate separation and flow from the inside to the outside of the cylindrical filter, according to an embodiment.

FIG. 19A and FIG. 19B illustrate a tubular or cylindrical separation system, closed at one end, with soluble matrix between a cylindrical filter and filter housing to facilitate separation and flow from the inside to the outside of the cylindrical filter and with the filtrate collecting or pooling in the bottom section of a tube, potentially in a drip-wise fashion, according to an embodiment.

FIGS. 22A and 22B illustrate a simplification of a microplate filtration system using a simplified microplate design and an absorbing material with a soluble matrix layer instead of a vacuum pump or centrifuge, according to an embodiment.

DETAILED DESCRIPTION

Figure 1:
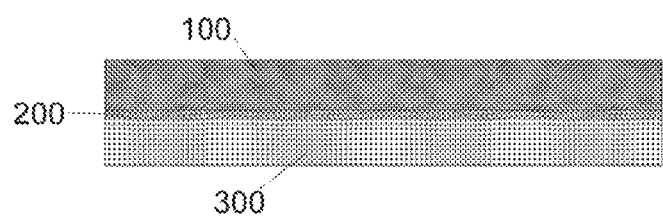
FIG. 1 illustrates a composite filter including the initial microporous filtration filter, a macroporous bottom support filter, and soluble matrix held within the pores of the bottom filter, but in contact with the bottom surface of the initial microporous filter, according to an embodiment.

Filters, filtration membranes, or membrane filters are all considered synonymous for the purpose of this disclosure. While some may argue there are differences, such as whether a filter is made of a non-woven material or woven material made of precisely arranged overlapping threads, or lithographically produced, man-made or natural, such distinctions are not made or recognized for the purpose of the below description. A more generic term of filter will be the primary word used. Furthermore, the type of filters discussed in this disclosure are those that are commonly used for biological sample processing, and not those that may be used in industrial or continuous filtration such as sand, diatomaceous earth, coarse metals screens and the like.

A filter is designed to separate a mixture, in the current disclosure, aqueous liquids. While this disclosure focuses on hydrophilic filters, the underlying concepts and principles of the disclosed technology are generally also applicable to hydrophobic filters and non-aqueous or non-polar liquids. A filter used for the purpose of separation or fractionation of a sample into a filtrate and retentate may be different from the term 'membrane' used by itself, which may be a porous paper, porous polymer, fibrous glass, or similar structure that primarily serves the purpose of supporting fluid and biomolecule flow, transport or interaction. It may also inadvertently contribute to separation, but that may not be its primary function. An exception to this is the term "plasma separation membrane (PSM)", which is intended to fractionate or separate blood into cellular and plasma fractions.

The separation properties of a filter may be based on particulate size, charge, or a combination of these factors. A filter may also possess biochemically functionalized components that capture or block specific components, e.g., causing agglutination, in which specific particles, such as cells, clump together, preventing their passage through the filter based on the increased size of the clump rather than the particle alone.

While filters are the primary separation mechanism under discussion, filtration may also be achieved by the use of microchannels of specific dimensions, and sometimes large microchannels leading to smaller microchannels, in an effort to mimic a planar filter. In some cases, the distinction between microchannels and filters becomes blurred, such as when considering a track-etched filter.

Hydrophilic filters are often characterized by the filter material type or composition (e.g., nitrocellulose, hydrophilic PVDF, PE, Nylon, etc.), filter thickness (e.g., 125 µm), pore size (equivalent or average pore diameter, e.g., 0.45 µm), bubble point, breakthrough pressure (e.g., 30 psi or 207 kPa), and flow rate at a given pressure (e.g., 40 µL/min/cm$^2$ at 10 psi or 69 kPa). Other characteristics may include retention parameters of certain key materials such as red blood cells or bacteria.

Breakthrough pressure is nearly equivalent to the bubble point if the same solution is used in both cases (e.g., water). The former is a factor of pushing liquid through a filter and the latter is a factor of pushing liquid out of a filter (using air). Both are functions of the capillary pressure equation which is dependent on pore size or equivalent pore diameter of the filter, contact angle of the filter with respect to the liquid used (hydrophilicity), and the surface tension of the liquid with respect to the ambient atmosphere, usually air.

Often the aqueous breakthrough pressure of a filter is much higher than a desired system flow pressure. Sometimes it is even higher than the pressure a desired filter or filter holder, fittings, or other connected components can withstand. To remedy this, one could replace the desired fittings, filter holder, etc. with alternative fittings that can withstand the high pressure that may be reached by first wetting through the filter. Alternatively, a filter is often wetted with solvent, which eliminates the capillary pressure by wetting through the filter easily, after which the aqueous solution can flow more freely according to established flow parameters. Established flow parameters, or steady-state flow conditions, refers to liquid flow that is already ongoing or established in a system, rather than the liquid passing through a system for the first time. Important system characteristics that are used to define established flow include liquid flow velocity, liquid viscosity, pressure gradients, and flow channel dimensions.

Sometimes, however, it is not possible or convenient to wet the filter with a solvent prior to use, such as if it is within an enclosed device. It may also be uneconomical, bulky, or otherwise undesirable to use high-pressure fittings. Also, depending on the application and design of the system, it may be desirable to use low pressure, such as what may be achieved by suction, to both wet through the filter, or initiate flow through the filter, and draw the bulk liquid through the filter such as for filtration purposes. Normally suction, when generated by electro/mechanical vacuum pumps, can only achieve a maximum suction pressure of 1 atm (14.7 psi or 101 kPa), and often much less. Mechanical suction alone, such as what may be achieved by a hand-held suction bulb, may only reach a few psi.

In some systems, such as in microfluidics, it may be inconvenient to apply any external pressure or vacuum forces at all: the filtration and processing system may, in this case, operate completely based on capillary-driven flow.

Suction, however, has a number of advantages for drawing liquids into or through a system, compared to positive pressure, such as what may be achieved by a syringe or syringe pump, or capillary-driven flow. Actuation of a suction bulb is typically much easier than actuation of a syringe. Mechanically, a suction bulb is typically simpler than a syringe, making it potentially easier and cheaper to manufacture. Also, with suction-driven flow, much larger liquid volumes may be processed than what may be practical with capillary flow.

The advantages of a syringe, on the other hand, are that a higher positive pressure can usually be generated compared to negative suction pressure of a suction bulb. Also, higher flow rates through a filter can be generated once flow is established, due to the higher pressures that can be generated, and, potentially, some degree of volume control is possible if the volume of liquid delivered by the syringe is carefully monitored. The advantage of capillary-driven flow is that the mechanics of the system can be very simple and automatic.

This disclosure describes various modifications to filters, filter housings, or microfluidic channels that eliminate the complication of high breakthrough pressure, or other high-pressure requirements. In various embodiments, these modifications actually eliminate any need for an additional pressure transient beyond normal desirable flow gradients. In some cases, there is no applied pressure gradient, and liquids are moved through a filter and subsequent downstream system merely by the use of capillary forces. These described modifications are useful because they eliminate the need for high pressure to initiate flow through a filter. Although there are many benefits associated with eliminating high pressure requirements, a particular benefit is that it allows suction to be more useful for flow control because it eliminates one of the disadvantages of suction flow (low pressure) and highlights its advantages (ease of use compared to a syringe and larger volumes compared to capillary-pressure-only systems).

Another benefit of the disclosed technology in relation to the processing of biological samples includes the fact that it allows relying on capillary forces alone to extract and collect filtrate, resulting in a device that is completely passive or automatic in its function, with no intervention or task required of the user to initiate or complete the filtration and collection process. This makes the device easy to use. Another benefit is that the capillary force that may be used for extraction and collection is a very low-pressure system compared to the high initial pressure spike needed in traditional systems. As cells are very fragile and subject to breakage or lysis, the low-pressure nature of the process results in cleaner filtrate, and more complete, viable and intact cells in the residue or fraction of inlet sample that does not pass through the filter. This results in a device that produces a superior product or output. Another benefit, due to the fact that high pressures are not involved and mechanical intervention of the user is not required, is that the device designed to perform the separation or filtration and collection can be much less mechanically demanding and complex, resulting in a device that is less expensive to manufacture and has fewer points of failure and is easier to operate than one that uses alternative methods.

Capillary pressure is often used to draw liquid through a system. Provided the drawing force of capillary pressure is greater than any backpressure that may be present, liquid can flow indefinitely. Backpressure may be generated in a capillary flow system, either at the leading or lagging end of liquid flow, if the liquid encounters a junction where the capillary pressure (as defined by the equation below) is higher in the system proximal to the junction (proximal meaning where the liquid already is) than it is at the junction, as defined by the new parameters of the new flow channel or system.

$$P = -\frac{2\sigma\cos\theta}{r},$$

where: P is capillary Pressure, r is the radius of the pore(s) or flow channel, $\theta$ is the contact angle of the filter material, and $\sigma$ is the surface tension of the liquid.

A negative pressure is similar to a suction force that draws a liquid into the system. A contact angle greater than 90° represents a hydrophobic material, and the resulting capillary pressure turns positive, indicating a positive force is required to push liquid into the system.

If only the radius of a flow channel changes, the pressure required to force a liquid past a junction is given by the equation—

$$\Delta P = P(r2) - P(r1) = \frac{2\sigma\cos\theta}{r1} - \frac{2\sigma\cos\theta}{r2} = 2\sigma\cos\theta x \frac{(r2-r1)}{r1r2},$$

where r1 is the radius of the flow channel proximal to the interface (where the liquid already is) and r2 is the radius of the new flow channel at the interface.

A positive $\Delta P$ indicates force, or pressure, is required to push a liquid past or through the junction. If $\Delta P$ is negative, the liquid will continue to flow on its own due to the capillary pressure of the new system at the interface being greater than the capillary pressure proximal to the interface. Capillary pressure can also be termed capillarity, so a filter or channel with a higher capillary pressure than a first filter or channel is said to have a higher capillarity than the first filter or channel. When a region of high capillarity interfaces with a region of low capillarity, a capillary stop junction is formed, and force is required to push liquid past the junction or interface of the two regions. A capillary stop junction may also be called, e.g., a capillary barrier, stop junction, pressure barrier, capillary stop, capillary stop valve, or microfluidic stop valve.

It is important to emphasize that the capillary pressure equation is dependent on an air/water (or gas/liquid) boundary where liquid is passing through a channel, filter, or system for the first time (leading end or edge of liquid flow) or where all liquid has passed through a system and is followed by air that is being reintroduced by the departure of the liquid (lagging end or edge of liquid flow), where a liquid surface tension is present. If no such boundary exits, capillary pressure is zero and flow is defined by established flow parameters, or steady-state conditions. A liquid surface tension may also exist between two dissimilar liquids, such as aqueous and organic liquids.

Liquid is drawn into a hydrophilic filter initially by capillary forces. It is difficult to force liquid out of, or through, a filter because at the distal (downstream) surface of the filter, or interface, the pores open to the larger flow system, such as a tube or pipe connected to the downstream end of the filter housing, or other flow channel geometry. Referring to the above capillary pressure equations, the radius of the flow system may change from, e.g., 0.1 µm to, e.g., 1 mm or 1 cm. In this case, the pressure to push liquid through this interface is roughly equivalent to the original capillary pressure (because 1 cm>>0.1 µm, P(1 cm)<<P(0.1 µm), so P(0.1 µm)–P(1 cm) (pressure to force a liquid past the junction)≈P(0.1 µm).

The situation and equations discussed above describe the case when considering the leading edge of liquid flow. Capillary forces may also be present at the lagging end of fluid flow, when all the liquid has flowed through a junction and an air/liquid condition is reestablished at that junction. This renewed capillary pressure can produce a backpressure on fluid flow and possibly stop flow if it is greater than the capillary pressure experienced at the leading edge of flow. Capillary backpressure caused by the lagging end of flow can become a significant issue when considering the amount of plasma that can be extracted from a plasma separation filter.

The reason a solvent (such as ethanol or acetone) is often used to eliminate high breakthrough pressure is because the surface tension (a) of many solvents is near zero. So, the effect of a radius change in a system when the surface tension of the liquid is near zero is relatively insignificant and the solvent can generally pass through the filter with little or no resistance. Once a liquid is on both sides of a junction, the capillary pressure is eliminated. Normally the primary liquid of interest is added to the system soon after the solvent is added and before the solvent dries: otherwise the capillary pressure of the filter may be reestablished. Although use of solvents to reduce the difficulty of passing an aqueous liquid through a filter is most common with hydrophobic filters, it may also be used when a hydrophilic filter has a very small pore size (e.g., <0.1 µm)

An example of a system with multiple junctions, where flow continues past these junctions with no applied force, is a lateral flow immuno-assay, or lateral flow test strip. In a lateral flow system, multiple filters or membranes or porous papers are layered on top of each other to facilitate certain functions important to the operation of the device. For example, an initial sample pad may have a layer that absorbs and distributes a blood sample across a filter that separates plasma from whole blood. The plasma is drawn through the filter by the higher-capillary pressure, or higher capillarity, of a membrane below the sample pad. This second membrane may have a higher or stronger capillarity due to any one of the reasons discussed above, e.g., due to a reduced pore diameter compared to the initial filter, or a lower contact angle or higher hydrophilicity compared to the initial filter.

In the second membrane, the liquid (e.g., plasma) may interact with a stored reagent (e.g., conjugate) important to the function of the test. The liquid then encounters a third junction (e.g., with a nitrocellulose membrane), where it continues to flow due to increased capillarity of this third membrane. The third (nitrocellulose) membrane may contain the test and control lines of printed biomolecules important to the function of the test. Finally, a fourth membrane is encountered, usually called the absorbing pad, that has the highest capillarity of all the materials, providing a strong driving force to pull the liquid through the entire system.

In the example above, liquid flows through multiple junctions due to increased capillarity of each new material, while, within the filter or material, the liquid flows due to the capillary pressure at the leading edge of flow where a liquid/air boundary is present. Once liquid has moved past a junction between two filters, the capillary forces present at that junction disappear, because the air/liquid interface has moved past the junction and a liquid/liquid condition is present at that junction. In this situation, the liquid is drawn through the junction due to the capillary forces some distance ahead, where the air/liquid boundary is present. The flow parameters at the junction are based on that downstream driving capillary pressure (or other drawing force, such as suction pressure generated by a suction bulb) and other established flow parameters.

Now consider a condition when the liquid has moved past the initial junction between two filters, or two porous surfaces, due to the increased capillarity of the second porous material. As has been explained, the capillary pressure at that junction has now disappeared, and the flow conditions at that point are defined by the downstream capillarity, or other drawing force or pressure gradient. Instead of a downstream drawing force (capillary or suction pressure), the flow conditions could also be determined by an upstream positive pressure, such as what may be exerted by the displacement of a plunger in a syringe. The important factor is that, once the liquid has moved past the junction, the capillary forces at that junction have vanished.

Passing the leading edge of liquid completely through a porous material, such that it exits the porous material on the opposite side of where it was delivered, is the definition of 'breakthrough' as used in the term "breakthrough pressure" and as generally used in this disclosure. However, in the case of the successive porous materials, no pressure was actually exerted in order to push the liquid past the junction; rather, it was the increased capillarity of the second porous material that drew the liquid through. In this manner, the high breakthrough pressure that may be indicated as a characteristic of the first filter did not actually become a factor. No excessive positive or negative pressure was exerted; only the natural capillary pressure of the second porous material was needed.

Now consider a situation where liquid has been drawn past a junction between an initial filter and a second porous material, due to the increased capillarity of the second material, and then the second material is physically removed from the system. Similar to the previous case, once liquid is past the junction, the capillary forces at that junction vanish, and flow out of the first filter continues to proceed according to established flow parameters, either due to a positive pressure on the liquid upstream of the junction, or a negative pressure downstream of the junction, such as what may be exerted by a suction bulb, or due to a secondary capillarity driving system such as small flow channels placed next to the second porous material that has since been removed.

Instead of removing the second porous material that has drawn the liquid past the junction, consider further a case where the second material dissolves in the liquid that has filled its porous structure. Similar to the case described above, because the liquid has already passed the junction, capillary pressure at that junction has already disappeared, no high breakthrough pressure was required, and flow may continue under established flow parameters either due to an upstream positive pressure or downstream negative pressure or another capillary driving system.

In this manner, by using a porous material that is made, at least in part, of a component that is soluble in a liquid passing through it, and placing it in physical contact with the downstream surface of an initial filter, which porous material, before the soluble component dissolves, possesses a higher capillarity than that of the initial filter, and which porous material after the soluble component dissolves, if any remains, represents no significant barrier to established flow, the initial filter's breakthrough pressure is effectively eliminated.

Although the nature of the liquid may have changed slightly by having a component of the second porous material become dissolved in it, this change can be tailored to be only a small change in surface tension (either increased or decreased) and/or only a slight change in viscosity (either increased or decreased), which are the liquid parameters important in governing established flow.

This new system may be described as a composite filter including multiple parts. An example three-component composite filter is illustrated in FIG. 1. The depicted composite filter includes an initial filter 100 which controls the filtration parameters; a porous soluble component or soluble matrix 200; and another material 300 with larger pore structure than the initial filter which serves to support or hold in place the soluble matrix 200 and put it in direct physical contact with the initial filter 100. Depending on the design of the system, the third component may not be needed, but if used, it controls the actual breakthrough pressure of the entire system.

The effective capillarity of the soluble porous material, or soluble matrix, must be higher than the capillarity of the initial filter. This higher capillarity, or ability to draw liquid past the capillary stop junction, can be based on the relevant parameters shown in the capillary force equation, but may also be due to the chemical nature of the soluble matrix, including its ability to generate osmotic forces and/or its hygroscopicity. After the liquid has entered the pores of the soluble matrix, the liquid is on both sides of the junction between the initial filter and soluble matrix, eliminating the capillary pressures at the junction and eliminate the breakthrough pressure of the initial filter. If this condition is not satisfied, such as if the soluble matrix dissolves in the liquid while the liquid is still within the initial filter and has not yet exited the initial filter or moved past the junction and into the matrix, which may take place if the soluble matrix is not porous or the liquid is pulled back into the initial filter, then the high breakthrough pressure of the initial filter still exists.

Provided no significant capillary pressure is present at the lagging end of liquid flow, the ongoing flow is determined by the new system where the soluble matrix has been placed. However, the capillarity of the initial filter can still be important if the lagging end of liquid flow, where a liquid/air interface exists, begins to enter the upper surface of the initial filter (e.g., all liquid placed on the initial filter has now entered the filter and is no longer pooled on the upper surface of the filter). In this case, the overall movement of filtrate is determined by a balance of the capillarity on the leading end of flow and backpressure that may be generated on the lagging end of flow.

In this case, flow through the filter may stop. However, in some designs, as discussed later in this disclosure, a venting duct may be present downstream of the initial filter so that filtrate that has already passed through the filter and into the area downstream of the filter may still be collected or moved forward by suction, capillary pressure, or positive pressure placed at the point of the venting duct rather than upstream of the filter where it could cause filter damage or cell lysis if whole blood is being filtered.

For the soluble matrix and this design to function properly, the initial filter and the downstream flow system where the soluble matrix is placed either are hydrophilic, or can be rendered hydrophilic by some secondary process such as UV or plasma treatment or film coating.

Figure 2A:
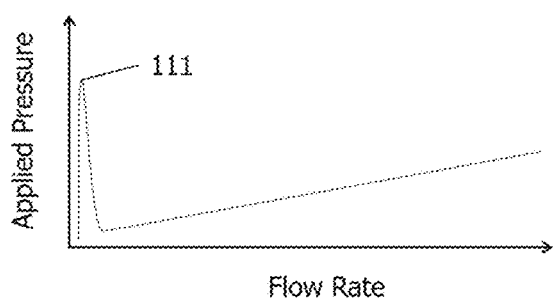
FIGS. 2A and 2B illustrate, in graphical form, how soluble matrix technology alters the pressure/flow rate profile of a filter from a traditional configuration with a high initial pressure spike constraint (FIG. 2A) to use in conjunction with a soluble matrix where no external pressure is applied or needed to initiate flow (FIG. 2B).
Figure 2B:
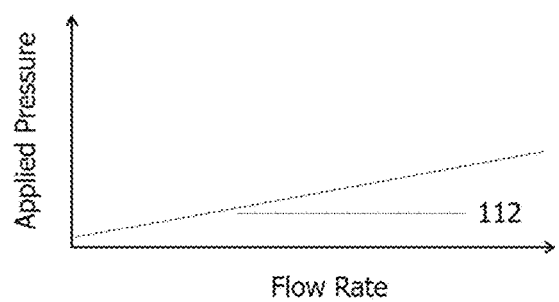

FIGS. 2A and 2B illustrates the phenomenon that has been discussed. FIG. 2A is a typical pressure versus flow rate profile of liquid passing through a filter. In general, the higher the pressure that is applied to the liquid, the higher the flow rate of filtrate that passes through it. However, this is the steady-state condition. Before the steady-state condition is reached, there is another condition where the initial flow of liquid passes completely through the filter for the first time. For the purposes of this disclosure, the initial flow of liquid is defined as the passage of filtrate completely through the thickness of the filter up to and including the emergence of the filtrate through the bottom surface or downstream surface of the filter.

To pass liquid completely through the filter for the first time, a different and much higher pressure, or pressure spike, is needed. This is the filter's breakthrough pressure, shown at 111, and is comparable to the pressure required to pass liquid through a capillary stop junction, as has been discussed.

FIG. 2B illustrates the relationship between pressure and flow rate in the condition where soluble matrix is used to initiate flow through a filter. As can be seen, the advantage of this method is that no pressure spike is involved to initiate flow, or the initial passage of filtrate completely through the filter. In some settings, such as in industrial filtration processes, the elimination of this spike may not be of any major benefit. However, in many other settings, such as in medical applications for the processing of biological samples, the elimination of this pressure spike offers many advantages, such as being able to use simple capillary pressures 112 to support continuation of flow through a filter and downstream processing system.

Micro/Nano Particle Soluble Component. The porous soluble component or soluble matrix may be a simple salt, such as sodium chloride (NaCl), or it may be a more complex organic salt, such as a low-viscosity cellulose salt or an anhydrous acid or base, such as ethylenediaminetetraacetic acid (EDTA), or it may be a sugar such as sucrose or dextrose, or sugar derivative such as Heparin. It may also be a soluble protein or other material. Some salts, sugars, proteins, or anhydrous acids or bases (collectively referred to as the soluble matrix) may be inappropriate for the filtrate being collected, or may impart undesirable features or components to the filtrate. However, some soluble components may be favorable, such as those that help preserve beneficial features of the filtrate, or do not interfere with downstream analysis or processing of the filtrate. Those of ordinary skill in the art will be able to select a suitable material for the soluble matrix based, e.g., on the type filtrate and use case, without undue experimentation.

In the case where the soluble matrix adds desirable features to the filtrate, the soluble matrix can be collected together with the filtrate for downstream processing. In the case where the soluble matrix interferes with downstream filtrate processing or analysis, it can be excluded from the volume of filtrate moved downstream or collected. How this portion of the filtrate can be excluded is discussed later in this disclosure.

It is also desirable that the soluble matrix, due to its placement in physical contact with the initial filter where it may be stored for a significant amount of time, is not reactive or damaging to the filter.

To form a micro- or nano-porous structure, the soluble matrix material may be ground to a very fine powder, in some embodiments. The porosity of the soluble matrix may be a factor of the spaces between the soluble material, rather than any actual porosity in the material itself. The important parameter of the soluble matrix is its capillarity compared to that of the initial filter, which may be a component of its grain size, but also of its material chemistry, including being hygroscopic or being able to generate osmotic forces to draw liquid past a capillary stop junction. The rate of dissolution of the soluble matrix in the filtrate of the initial filter, which depends on chemistry and grain size, is also an important consideration. Those of ordinary skill in the art will know how to optimize the soluble matrix according to the needs of the system.

In some embodiments, the soluble matrix comprises both soluble and insoluble materials, where the insoluble material is held together by the soluble material. In this case, the combined material may disintegrate when exposed to the filtrate rather than actually have a significant amount of the material dissolve in the filtrate. An example of this may be an insoluble neutral and non-reactive polymer powder bound together by soluble sugar linkages. Once wetted by the filtrate, the matrix may disintegrate, which can serve basically the same function as dissolving, provided the disintegrated material does not represent a barrier to or interfere with downstream flow or processing of the filtrate.

The soluble matrix can be generated by mixing the components of the matrix in a solvent that only weakly dissolves the material, or weakly dissolves only the soluble component of the material. For example, if the matrix is made of a simple sugar, then a solvent, such as anhydrous acetone or ethanol that does not significantly dissolve the sugar, may be combined with 1 or 2% water, which does dissolve the sugar. The resulting mixture or solvent and powder can be described as a slurry. A very small portion of the sugar slurry does dissolve in the solvent, but most of it remains undissolved. When the solvent evaporates, the remaining material is a semi-pliable porous material that can be placed in the appropriate position in physical contact with the initial filter. In another example, the matrix may include or consist of an insoluble powder and a small amount of soluble sugar, to which water is added. The sugar dissolves in the water, but the insoluble powder does not dissolve, and the mixture again forms a slurry. When the water evaporates, the insoluble powder is bound together by the sugar that has dried on its surface and formed connections or bridges between the powder particulates. Again, this matrix can be placed in its desired position in physical contact with the bottom surface of the initial filter and the upper surface of the base material.

Before the solvent evaporates from the slurry, the slurry can be pressed into a film of desirable thickness. Alternatively, the slurry or matrix may be spin-dried into a thin film, which may be useful for some designs, as it uses an established processing technology (familiar from the semiconductor industry, where thin films of resist are often spun onto semiconductor substrates). The soluble matrix may also be spin-dried into a fibrous material that can be collected as a type of fibrous filter that is pressed to the appropriate thickness and cut to size.

Preferably, the material used for the soluble matrix does not swell significantly in the presence of the filtrate (i.e., does not absorb the filtrate rather than dissolving in it), avoiding potential damage to the initial filter that may otherwise result. Further, the soluble matrix may be hygroscopic, which may add some desirable feature to the soluble matrix, but not too hygroscopic. Hygroscopic materials tend to be difficult to preserve and store, and many hygroscopic materials can absorb a significant amount of liquid before dissolving in it. Therefore, the soluble matrix is preferably only slightly (if at all) hygroscopic.

Figure 3A:
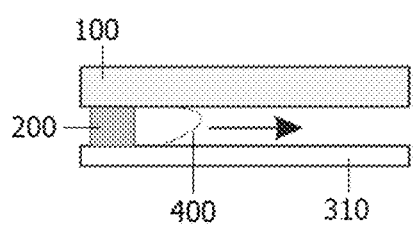
FIGS. 3A and 3B illustrate a simplified version of a composite filter device in a horizontal and vertical orientations, respectively, where the soluble matrix is held in contact with a portion of the bottom surface of the filter and within a flow channel for the filtrate once it passes through the filter, according to an embodiment.

Minimizing the Amount of Soluble Matrix. The mechanism of action to eliminate the breakthrough pressure of the initial filter is to use the higher capillarity of the soluble matrix to cause the filtrate to break through the downstream or bottom surface of the initial filter, and then have the capillary pressure inherent to the soluble matrix disappear by the soluble matrix dissolving in the filtrate. As has been explained, the breakthrough pressure caused by the capillary pressure of the initial filter disappears because filtrate is now on both sides of the junction between the bottom surface of the initial filter and whatever is immediately adjacent to it. However, consider a condition when filtrate has broken through the downstream surface of the initial filter in only one location. As this filtrate passes through the initial filter at this location, it may spread out and travel along the downstream surface of the initial filter. This is illustrated in FIGS. 3A (horizontal) and 3B (vertical). The driving force of this spreading is the hydrophilic nature of the downstream or bottom surface of the initial filter 100 and the hydrophilicity of the base material 310, and the formation of a meniscus 400 between these surfaces. This spreading is not caused, or not to a large degree, by the continuation of flow of filtrate through the initial filter at the one location where the soluble matrix 200 was present, but by the whole bottom surface of the initial filter 100 being saturated with filtrate that is waiting to penetrate the last few micrometers of the bottom porous structure of the initial filter 100. The spreading meniscus 400 formed between the bottom surface of the initial filter 100 and the upper surface of the base material 310 can be enough to bridge this final gap in flow of the filtrate waiting to break through the bottom surface of the initial filter 100. This is done by wetting through this final gap from the side of the filter where the meniscus 400 is present. The meniscus 400 moves or flows tangentially across the whole bottom surface of the initial filter 100 not because of continued flow through the initial breakthrough point, but because of flow normal to the surface of the initial filter 100 that simply adds to the volume of filtrate that has passed through the filter and causes the meniscus 400 to spread.

This spread initiates at the point of the soluble matrix 200 and moves outward or away from this point depending on the structure of the open area between the bottom surface of the initial filter 100 and the base material 310. In this manner, the total surface area of filtration can be increased without necessarily increasing the amount of soluble matrix 200 used for the system to function.

Plasma Separation from Whole Blood. Referring again to FIGS. 3A and 3B, an example of one embodiment of a composite filter system is a plasma separation device that uses, as the initial filter 100, the Pall Vivid Plasma Separation Membrane (PSM) with a minimum, or bottom, pore diameter of between 0.5 and 1.2 µm. The soluble matrix 200 may be a finely ground EDTA powder placed between the bottom surface of the PSM 100 and the top surface of the base material 310, which may be polyethylene terephthalate, or PET. The thickness of the soluble matrix 200 between the surfaces may be between 25 and 1,000 µm, or preferably between 100 and 200 µm, defined by an adhesive layer connecting the PSM 100 to the base material 310 (not shown in FIGS. 3A and 3B, but illustrated in later figures). The porosity, or approximate pore size, of the soluble matrix 200 may be between 0.01 and 0.4 µm. This small pore diameter, compared with that of the PSM 100, together with the material composition, creates a region of higher capillarity than that of the PSM 100; thus, plasma passes into the soluble matrix 200 and out of the PSM 100.

It is important that the plasma passes all the way through the soluble matrix 200 such that is contacts the bottom surface of the new flow system (the base material 310) before the soluble matrix dissolves. If the plasma does not reach both surfaces, and remain in contact with both surfaces, a meniscus 400 bound by both surfaces will not be formed. This meniscus 400, however, is what allows the downstream capillarity of the system to be able to cause the plasma to continue to flow.

Once the soluble matrix 200 has dissolved, the capillarity of the new flow geometry takes over and governs continued flow, until the time when capillary pressure of enough significance is generated at the lagging end of liquid flow, which would be the liquid remaining in the PSM 100, which could stop further flow as has been discussed.

The amount of plasma collected from a PSM is directly proportional to the amount of blood added and surface area of PSM used. As has just been described, an increase in the surface area of the PSM may not necessarily require an increase in the amount of soluble matrix used. The composite structure can be designed such that the total surface area of contact between the PSM and the soluble matrix, is kept low, as is illustrated in FIGS. 3A and 3B.

Figure 3B:
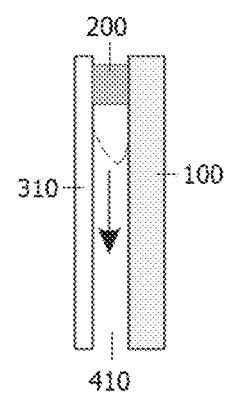
Figures 4A, 4B, 4C:
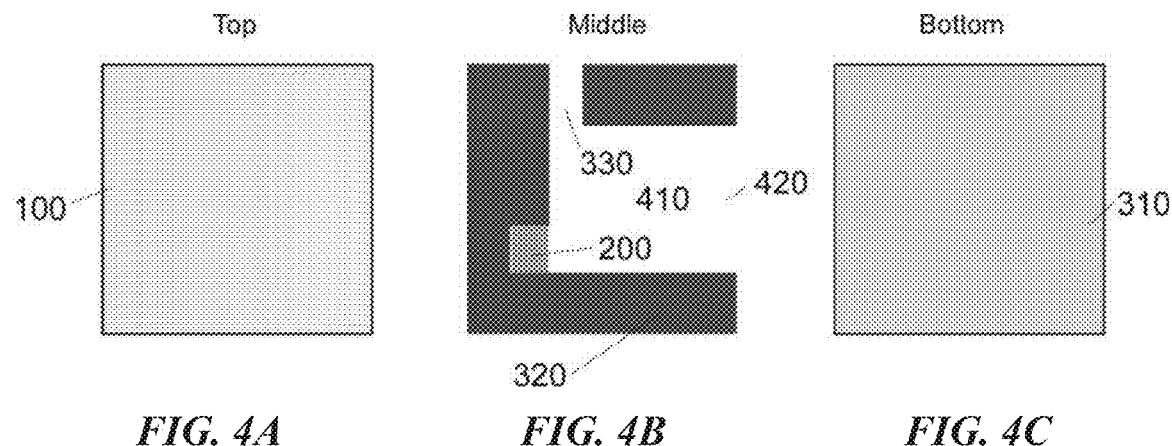
FIGS. 4A-4C illustrate, in parallel top, cross-sectional, and bottom views, a device where, by the strategic placement of a venting duct, the soluble matrix that initiates flow of filtrate through a filter can be excluded from the volume of filtrate that is extracted or collected from a filtration device, according to an embodiment.

Exclusion of the soluble matrix from the Collected Filtrate FIGS. 4A-4C provide a layer-by-layer view of the device of FIGS. 3A and 3B, but also show additional features not illustrated in FIGS. 3A and 3B, namely the presence and placement of a venting duct 330 and adhesive support or wall structure 320 supporting the filter 100. If filtrate breaks through an initial filter 100 by passing into the soluble matrix 200 due to the soluble matrix's high capillarity, it may generate the meniscus between the initial filter 100 and the base material 310, as has been discussed. This meniscus 400 may spread through the entire open area 410 under the initial filter 100. However, although the meniscus 400 has spread, there may be no or very little movement of the portion of the filtrate that actually passed through the initial filter 100 and dissolved the soluble matrix 200. As was explained, the meniscus 400 spread is due to the expansion of the surface area of the initial filter 100 where filtrate was passing through. Except by the process of diffusion, the initial filtrate that passed through at the point of the soluble matrix has not moved, nor has the soluble matrix 200 moved, other than by dissolving in the filtrate and undergoing very small movement driven by diffusion and very little continued flow at this one point on the filter. The filtrate at this point has a high concentration of soluble matrix, and the filtrate in all other areas under the initial filter 100 has very little or no soluble matrix in it.

Consider a case where it is desired to extract the filtrate that has passed through the initial filter 100, either by downstream capillary forces or suction or another driving force. Due to the balance of capillary forces downstream of the filter and within the filter caused by the presence of the air/liquid interface of the lagging end of liquid flow, without the presence of a venting duct 330, it would be very difficult to extract any more filtrate out of the filter 100 to allow continued flow of the filtrate that has already passed through the filter 100 to be moved further downstream. In the case of a PSM, the pores of the filter would also be clogged with cells, making further flow through the filter difficult. With the presence of the venting duct 330, the filtrate can move forward, evacuating the area underneath the filter 100, with the space that was previously filled with filtrate now replaced with air (or something else) that has entered through the venting duct 330.

However, by the strategic placement of the soluble matrix 200, and the strategic placement of the venting duct 330, as shown in FIGS. 4A-4C, the volume of filtrate that has a high concentration of the soluble matrix 200 can be excluded from the volume of filtrate that is moved downstream, either by suction or capillary force at the point of filtrate extraction 420, or positive pressure exerted at the point of the venting duct 330.

Figures 5A, 5B, 5C:
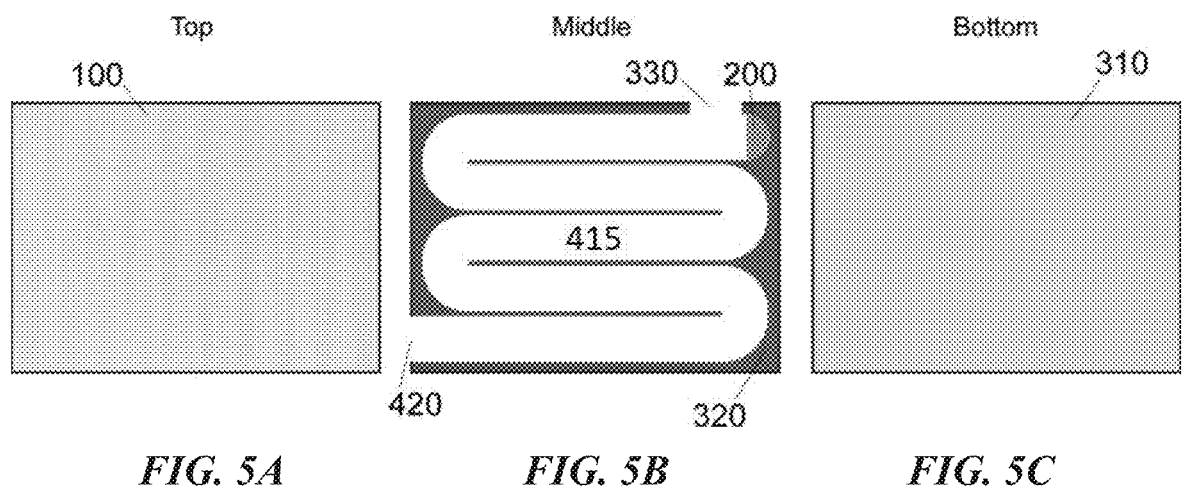
FIGS. 5A-5C illustrate, in parallel top, cross-sectional, and bottom views, a large-surface-area filter used for collecting a large volume of filtrate from a large input sample, and the implementation of a venting duct and serpentine channel for collecting the filtrate, according to an embodiment.

This is further illustrated in FIGS. 5A-5C, which show a device with a serpentine channel 415 formed in the adhesive support or wall structure 320 that covers a large portion of the bottom surface area of the initial filter 100. The serpentine channel 415 may be helpful for ensuring that no bubbles are trapped underneath a large surface area system, when the filtrate is collected or moved downstream of the initial filter 100. As is illustrated, the area of the soluble matrix 200 does not contribute to the volume of filtrate between the venting duct 330 and the filtrate collection point 420, but is effectively bypassed. This area would be included if the venting duct 330, as shown in FIG. 5B, were immediately to the right of the soluble matrix 200, but it is not. It is to the left and above the point of the soluble matrix 200; thus, the volume of filtrate that has passed through the initial filter 100 at that point remains under the filter and is not moved downstream of the filter.

When liquid is added to the upper surface of the initial filter 100, it preferably covers and saturates the entire surface of the filter 100. The capillarity of the filter is significant, and still plays a role in liquid movement once filtrate has passed through the filter, even if the filtrate has spread significantly underneath the filter 100. It is entirely possible, and has been observed, that if the filter 100 is not completely covered and saturated, filtrate that has passed through the filter 100 at one point can be drawn back into the filter 100 at another point where the high capillarity of the filter 100 may still exist, due to the fact that the filter 10 at that other point has not been saturated. In the example of plasma separation from whole blood discussed previously, the capillarity of the bottom surface of the PSM is governed by flow channels within the range of 0.5 and 1.2 $\mu$m in diameter, whereas the effective diameter of the flow channel under the PSM is closer to the range from 25 to 250 $\mu$m. In this case, plasma will be drawn back into the PSM if its upper surface is not covered and saturated with whole blood.

Blood may be aided in its distribution across the top surface of a PSM by a close-fitting cover made of a hydrophilic material that aids in channeling the blood by capillary action across the whole PSM surface rather than pooling at only one location where the blood may be introduced. This is illustrated in later figures.

There are many possible configurations and geometries of the initial filter, microchannel, and soluble matrix; many possible soluble matrices can be used; and many possible applications can be developed. Whether it is plasma that is produced, or another subcomponent of whole blood, or a subcomponent of any other liquid sample added to the initial filter depends on the specifications of the filter used. Applications are discussed below and include microplate filtration, large-volume filtration of whole blood to plasma, an integrated device for small-volume plasma separation from whole blood using capillary-driven flow, a 'stand-alone' whole-blood hematocrit measurement device, a method of removing plasma for the collection of blood cellular components, a tool for automatic input-sample volume metering, and a method of overcoming the capillary stop junctions of one or multiple small microfluidic channels.

Whole Blood Filtration Cartridge. In the design for large-volume whole-blood filtration, the total blood volume may be around 300 to 1000 $\mu$L, with the collected plasma volume around 50 to 300 $\mu$L. In this case, the plasma filtrate could be collected in a specimen chamber to be used later for multiple diagnostics, or it could be re-deposited directly into a diagnostic system, or mixed with other reagents and stored or immediately used. The value of suction over capillary-driven flow is that it can facilitate larger flow rates for faster collection and can overcome small capillary stop junction pressures for collection into a large diameter collection vessel (large compared to the dimensions of the flow channel underneath the plasma separation filter).

This design is illustrated in FIGS. 5A-5C and FIG. 6. A PSM 100 with large surface area, such as around 10 cm of the Pall Vivid GR PSM, is used. As shown in FIG. 5B, an adhesive spacer serving as the wall structure 320, between 25 and 1,000 $\mu$m thick, or preferably between 100 and 200 $\mu$m thick, is used to form a serpentine channel 415 winding back and forth underneath the PSM 100. This is done to ensure no bubbles are trapped underneath the PSM 100 while the meniscus moves forward from the point of the soluble matrix 200 to the point of plasma collection 420. The serpentine channel 415 is also used to ensure no liquid is trapped as the plasma is extracted from the point of the venting duct 330 to the point of plasma collection 420. The actual width of the serpentine channel 415 can be optimized empirically, but is usually around 0.5-4 mm. The thickness of the walls of the serpentine channel 415, formed by the adhesive spacer 320, is minimized so that the spacer 320 can still support the PSM 100, but also allow the maximum possible surface area of the PSM 100 to be exposed to the open area of plasma collection 410. The venting duct 330 is placed in a strategic location to maximize the collection of plasma, but also to prevent the plasma with a high concentration of soluble matrix 200 from being collected, if it is not desired.

Figure 6:
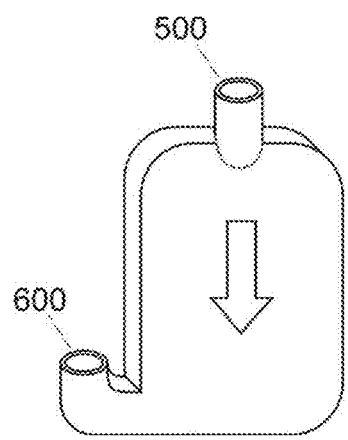
FIG. 6 illustrates a cartridge, in according with an embodiment, for extracting a filtrate, such as plasma, from a complex liquid sample, such as whole blood, with a sample inlet port and a filtrate or plasma collection fitting. The arrow shows the direction of filtrate flow. The filtrate collection device may use suction to aid in collecting the filtrate from the cartridge according to an embodiment.

FIG. 6 is a macroscopic view of the separation device of FIGS. 5A-5C formed in the shape of a cartridge with fittings for whole blood introduction and plasma extraction, respectively. When a whole blood sample is connected to the cartridge input 50, the blood enters the cartridge by gravity, positive pressure, suction, or capillary force. Once within the cartridge, blood spreads across the whole surface area of the PSM 100 by capillary force. Once plasma has spread through the serpentine channel 415 underneath the PSM 100, by the mechanism that has been explained, it can be collected into a vessel connected to the cartridge output 600.

The collection point of the cartridge output 600 is connected via a flow channel to the plasma collection point 420 at the end of the serpentine channel 415 shown in FIG. 5B. The plasma can be pushed into the collection vessel by positive pressure applied at the point of the venting duct 330, or it can be drawn into the collection vessel by suction pressure applied by the collection vessel itself, or something connected to the collection vessel.

Provided any applied air pressures are kept low, air will not pass through the PSM 100 when suction or positive pressure is applied to the serpentine channel 415 because the dimensions of the serpentine channel 415, with an effective diameter of between 25 and 1,000 $\mu$m, or preferably between 100 and 200 $\mu$m, compared to the pore diameter of the PSM being within the range of 0.5 and 1.2 $\mu$m and partially clogged with blood cells, cause flow to be much easier to pass through the channel 415 rather than through the PSM. If the pressure generated to push or suck liquid through the serpentine channel 415 is only in the few psi range, air will not be pushed through the PSM 100.

Integrated Plasma Separation from Whole Blood. FIGS. 3A-3B and 4A-4C illustrate a small-volume plasma separation device capable of integration into a microfluidic-based or membrane-based diagnostic system. An integrated plasma separation system may include multi-layered system where the PSM 100 is cut to the appropriate size and is held by an adhesive support or wall structure 320 underneath. The adhesive support 320 may be a layer between 25 and 1,000 µm thick, or preferably between 100 and 200 µm thick. If the adhesive support 302 is thicker than 1,000 µm, it may be difficult for a meniscus 400 that bridges the gap between the PSM 100 and the base material 310 to form. This meniscus 400, however, is important for the separation to proceed.

After blood is placed on the upper surface of the PSM 100, it spreads across the whole PSM 100 by wicking or capillary action, possibly assisted by a close-fitting hydrophilic cover illustrated in later figures. The PSM 100 becomes saturated with the blood sample, which is drawn through its pores by internal capillary forces. The high capillarity of the soluble matrix 200 underneath the PSM 100 draws the plasma through the PSM 100 at the point of contact. The plasma fills the pores of the soluble matrix 200 and touches the base material 310. The soluble matrix 200 can be held in place under the PSM 100 by placing it between the PSM 100 and the base material 310 and/or by placing it in contact with the adhesive support 320 that forms the walls of the space under the PSM 100.

As the soluble matrix 200 dissolves or disintegrates by dissolution of a part or all of the soluble matrix 200 by the plasma that has filled its pores, a liquid bridge or meniscus 400 is formed between the PSM 100 and the base material 310. As more plasma passes through the PSM 100 at the point of the liquid bridge or meniscus 400, the meniscus expands, breaking the capillary barrier along the bottom of the PSM 100 as it moves. Eventually, the entire open area 410 under the PSM 100 may be filled with plasma that has passed through the PSM 100.

At the plasma collection point 420 as shown in FIGS. 4A-4C and 5A-5C, another microchannel may be present (not shown) that is smaller in effective diameter than the space under the PSM 100. Alternatively, another filter or membrane may be present instead of a microchannel, which filter or membrane possesses higher capillarity than the space 410 under the PSM 100. Plasma may continue to flow into this microchannel or filter as the volume of plasma passing through the PSM 100 expands. If the movement of filtrate has stopped, due to the action of backpressure capillary forces caused by the lagging end of blood flow entering the smaller pores of the PSM 100, the plasma may continue flowing into the new microchannel or filter due to presence of the venting duct 330, which allows the plasma under the PSM 100 to be vacated by allowing air, or another material, to replace it. As has been discussed, the strategic placement of this venting duct 330, together with the strategic placement of the soluble matrix 200 which initiated the breakthrough process, can allow the volume of plasma with a high concentration of the soluble matrix to be excluded from the volume of plasma that is moved downstream of the PSM 100. Thus, an effective integrated plasma separation system is achieved with potential interface to a microchannel or new filter or membrane-based system.

Figure 7:
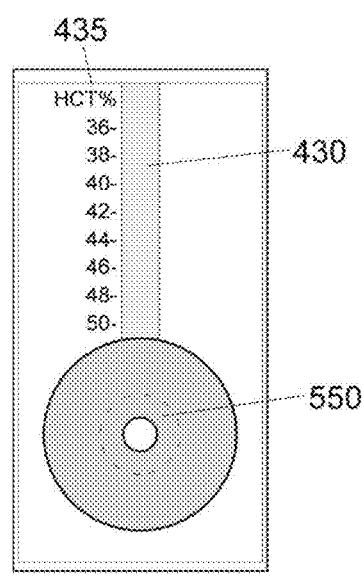
FIG. 7 illustrates a disposable hematocrit measurement device made possible by the plasma separation technology discussed in this disclosure, according to an embodiment.
Figure 8:
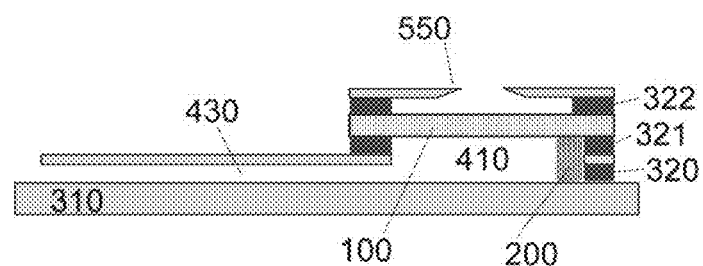
FIG. 8 illustrates, in a side view, layers of a disposable hematocrit measurement device, according to an embodiment.
Figure 9:
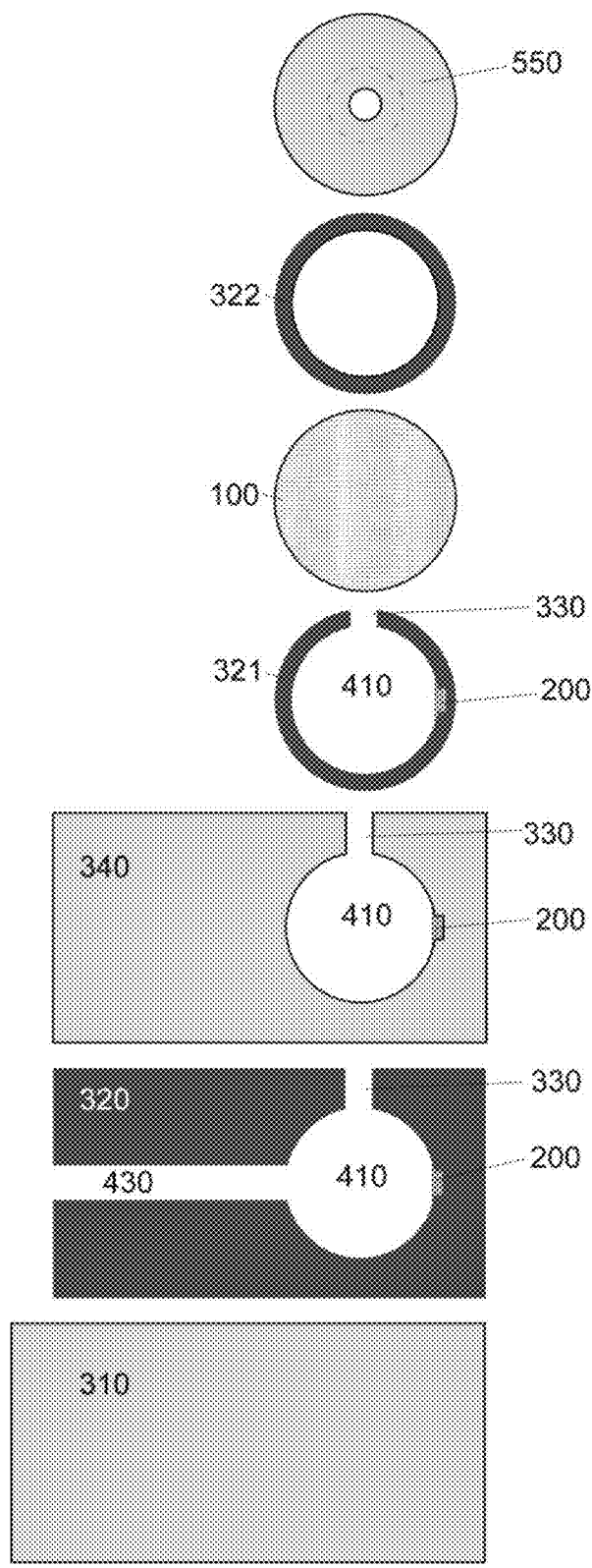
FIG. 9 illustrates a layer-by-layer detail of the components of a disposable hematocrit measurement device, according to an embodiment.

Stand-Alone Hematocrit Test Kit. FIGS. 7, 8, and 9 and illustrate the components and design of an integrated, analog, disposable hematocrit test kit (HCT) in accordance with one embodiment. The function and operation of the HCT is as has been described in the integrated plasma separation kit discussed above, although in the figures a lid 550 and lid spacer 322 are shown, which are not included in the previous figures. Also shown is the microchannel 430 placed at the plasma collection point 420 under the PSM 100, bordered on the bottom by the base material 310, top by the channel cover 340, and sides by the adhesive support 320. Rather than connecting to a downstream processing or detection system, as would be the case in an integrated microfluidic diagnostic system, the function of the microchannel 430 in this case is to allow the plasma that has been generated to be measured; this measurement is directly proportional to the hematocrit level in the blood sample used. This is true if, in all cases, the volume of blood applied to the PSM 100 is exact and remains constant from test to test, and the surface area of the PSM 100 remains constant and is exact from test to test. This also assumes that the separation and other characteristics of the PSM 100 remain constant from test to test, which can be quality controlled and guaranteed by the PSM 100 manufacturer and again by the kit manufacturer.

When the surface area and specifications of the PSM 100 remain constant, and the volume of blood delivered to the HCT kit is repeatable, then the volume of plasma produced by the HCT kit is directly proportional to its hematocrit level. This can be measured by how far the plasma moves up the microchannel 430, as measured by the measurement column 435 as shown in FIG. 7.

If a venting duct 330 is used, as is shown in the layer-by-layer illustration in FIG. 9, then the plasma produced that has filled the open area 410 underneath the filter 100 (hereinafter also "pooling area" 410) will move into the column 430, and the design has changed to a plasma separation and metering device with an interface to a microchannel 430 for downstream processing rather than a hematocrit measurement test kit because the amount of plasma generated is only enough to fill the pooling area 410, rather than maximizing the amount of plasma drawn through the PSM 100, which would be the case if no vent 330 is present. If the thickness of the adhesive layers 320, 321 and 322 is kept very small and no venting duct is present, some plasma will remain under the PSM 100, but a significant portion will pass into the channel area 430 for hematocrit measurement.

As plasma is mostly clear, rather than opaque red like whole blood, it may be difficult to see visibly in the hematocrit measurement column 435, which is likely made of clear plastic layers. In this case, it may be helpful if some contrasting agent or method is used, such as a dye or paper that changes color when wetted, a matte or translucent surface finish that turns clear when wetted, or something similar. It is also helpful if the leading edge of plasma flow within the measurement channel 430 is marked, such as by a color change, in the case that the leading edge retreats slightly back down the column due to evaporation, leakage, or another process. Also, in comparing FIGS. 8 and 9, it can be seen that the venting duct 330 (if used), soluble matrix 200, and plasma pooling area 410 span multiple layers and are not meant to be individual components within these layers.

Collection of Blood Cellular Components. Cell Sorting or Flow cytometry Application. One of the reasons for separating whole blood into its components is so that these components may be studied separately. While this disclosure focuses on the use of plasma extracted from whole blood, once that plasma has been extracted, the cellular components could also be studied. If an asymmetric PSM is used, the platelets will be trapped deep within the body of the filter. The red cells may also be difficult to retrieve; however, the larger white cells should mostly be accumulated either on the surface, or only shallowly buried within the filter, and could be removed by scraping the surface of the PSM to collect the material on top.

Instead of using an asymmetric PSM, it is possible to use multiple thin filters, with successively smaller pore sizes, which pore sizes are designed for trapping the majority of a specific cell type within the same size range. This way, each filter containing cells of a particular size range can be removed and extracted, such as by back-flow of liquid through the filter, and studied separately.

Referring again to FIG. 1, usually liquid can move from larger-pore to smaller-pore-sized filters, especially if the filters are of the same material, by passive capillary forces. Smaller-pore-sized filters usually translate into higher capillarity drawing liquid into them, if they are hydrophilic. However, if a large sample volume is used, or a sample is followed by a wash solution, there may be too much liquid for a few layers of filters to absorb. In this case, and is illustrated as filter 300 in FIG. 1, it may be useful for an inexpensive and relatively large-pore-sized depth filter to be used to absorb all excess liquid. The interface between a small-pore-sized filter, such as 100, and the depth filter 300 would be the soluble matrix 200, to facilitate movement of the liquid into the depth filter 300. An example of a depth filter is a thick glass-fiber woven filter around 600 to 1500 μm thick with nominal pore size between 1 and 3 μm made, e.g., by Pall Corporation, SKC Inc., Millipore and others.

Allowing excess liquid to drain through multiple filters and into a depth filter by passive capillary action can allow for easier retrieval or elution of viable cells within or on top of the filters, as compared with the case where the excess solution is forced through, such as by positive pressure applied with a syringe.

Automatic Input Sample Volume Metering. In the stand-alone HCT measurement application, it was discussed that the volume of blood delivered to the PSM 100 should be remain constant and repeatable from test to test. This volume can be controlled and exactly metered by use of a precision pipetting system, such as by pipetting an exact volume of whole blood from a blood specimen container and placing it in the kit. This volume can also be controlled by using an exact, automatic input-sample volume metering tool made possible by another implementation of the same soluble matrix that has been discussed. This device is illustrated in FIG. 10.

Capillary forces are automatic. An exact volume of sample, of blood or any other aqueous liquid, can be collected by touching a precisely dimensioned (cut to length) capillary tube to the sample to be measured. Assuming enough sample exists to fill the tube, the tube will fill automatically by the liquid passing through the inside channel until it reaches the open end of the tube on the opposite side of where the sample is introduced. The open end of the tube represents a capillary stop junction. It does not actually need to be completely open, but the diameter of any enclosure downstream of the tube needs to be larger in effective diameter than the capillary tube itself.

Figure 10:
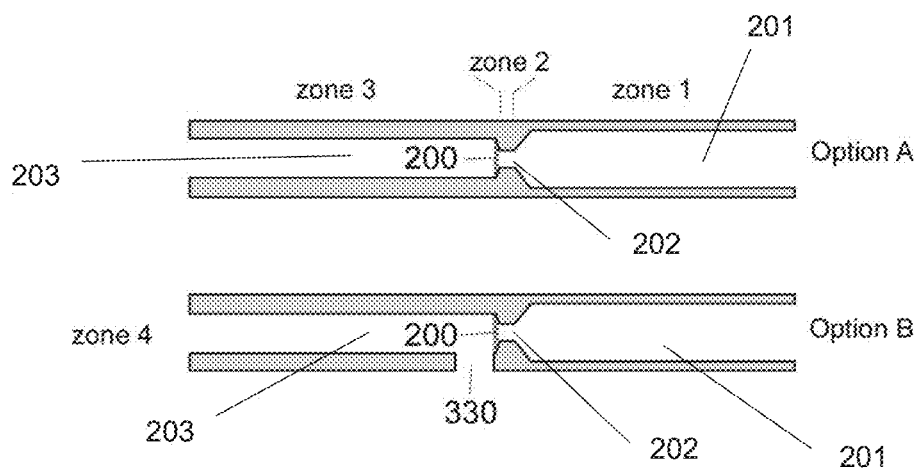
FIG. 10 illustrates two versions of, or options for, the design of an automatic input sample volume metering device made possible by the technology discussed in this disclosure, according to an embodiment.

With reference to FIG. 10, instead of a single capillary of one uniform diameter, consider a capillary with an initial diameter A1 (201), leading to another very short section of the tube with a smaller diameter A2 (202), which then leads to another section, with diameter between A1 (201) and A2 (202), called A3 (203). This is illustrated as Option A in FIG. 10 and labeled as zone 1 (for the section with diameter A1), zone 2 (with diameter A2) and zone 3 (with diameter A3, where A2<A3<A1, respectively).

The flow of liquid, such as blood, when the capillary tube is placed in contact with the liquid at the open end of zone 1, will be to automatically fill zone 1 and zone 2, and stop at the intersection between zone 2 and zone 3, where the smaller diameter A2 (202) opens up to the larger diameter A3. This enlargement of the channel diameter represents a capillary stop junction, as has been explained. Once flow has stopped at this point, the capillary tube is removed from the liquid source. The filling process should only take 1-3 seconds, after which the liquid source is removed.

If soluble matrix 200 in the form of a thin section of soluble matrix is placed at the junction between zone 2 and zone 3, the liquid that has stopped at this point will fill the pores of the soluble matrix 200 and move past the junction, filling the initial section of zone 3. At this time, the stopping force of the capillary stop junction is overcome by the increased capillarity of the soluble matrix 200. Since liquid (blood) is now on both sides of the stop junction, the capillary forces that held the liquid at that point vanish. Because the capillarity of zone 3 is higher than the capillarity of zone 1 (smaller diameter), the liquid volume in zone 1 will pass into zone 3 by capillary action. The liquid will fill zone 3 until, either, it reaches the end of zone 3 where another stop junction is present, or the lagging end of flow reaches the junction of zone 2 and zone 1, where a strong capillary pressure is re-introduced.

In this example, the volume encompassing zone 1 is the metered volume of sample which has been automatically metered and delivered into zone 3, assuming zone 3 is large enough to accept the entire zone 1 volume. The volume of zone 2 represents a dead volume which is held within the inlet port and not passed on.

In most applications, zone 3 is actually not a part of the capillary tube inlet, but is actually the first section of the downstream device, such as the plasma separation membrane 100 of the HCT test kit. Referring to FIG. 8, the inlet hole and cover 550, together with the adhesive spacer 322 and upper surface of the PSM 100, can be designed to have a higher capillarity than zone 1 of the metering tool.

It is possible that this HCT input section, or any input component of an integrated device, could have a higher capillarity than zone 2 of the metering tool. If this is true, then the metered volume is a combination of the volumes of zone 1 and 2, for the device to function, however, the input section has a higher capillarity than at least zone 1.

In the case where the high capillarity of zone 2 represents a barrier to ongoing flow of liquid through the system, such as into zone 4 of Option B, Option B may be a better design where the high capillarity of zone 2 can be bypassed by the presence of a venting duct 330 at the inlet side of zone 3. In this design, the high capillarity of zone 2 does not prevent flow of liquid further downstream of the metering tool. However, the capillarity of zone 3 could still be a limiting factor, depending on the overall design of the downstream portion of the kit.

This metering tool is useful for any aqueous liquid. However, due to the fact that blood is a very viscous and complex liquid, it is important to design the soluble matrix 200 such that it does not stop the flow of blood altogether. The porosity of the soluble matrix 200 can be quite large in this case, compared to the porosity of the soluble component in the plasma separation design. For example, if the diameter of zone 2 is around 100 μm, then the average pore diameter of the soluble matrix 200 could be up to 50 μm, compared to 0.5 μm as it may be in the plasma separation application.

Also, whereas the thickness of the soluble matrix 200 in the plasma separation application illustrated in FIG. 8 should span the entire gap between the PSM 100 and the top of the base material 310, in the case of the metering tool soluble matrix 200, it should be as thin as possible, such as 10-50 μm. However, the majority of the material making up the soluble matrix will be passed downstream in the liquid (e.g., blood), and, in this application, cannot be bypassed as it is in the plasma separation application.

Microchannel Capillary Re-Set. While the example above illustrated the use of the soluble matrix to overcome a single capillary stop junction to aid in automatic metering, a related design can be used to overcome capillary stop junctions of multiple small microchannels. This is achieved by using the soluble matrix to overcome, first, a single capillary stop junction, and then using the flow generated by this process to wet through the capillary stop junctions in following microchannels connected to the same collection channel. This is illustrated in FIG. 11.

Figure 11:
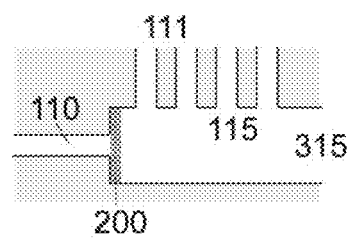
FIG. 11 illustrates a microfluidic channel embodiment where multiple small channels of high capillarity empty into a single larger channel of lower capillarity.

In FIG. 11, a soluble matrix 200 is in physical contact with the exterior surface of a capillary stop junction of one microchannel 110. As in the previous example, this allows flow to proceed past this stop junction and into the collection channel 315. One or more additional small microchannels 111 may also be present, connected to the collection channel 315. At the interface of connection of these smaller microchannels 111 to the collection channel 315, capillary stop junctions are present 115. As liquid flows through the initial channel 110 and into the collection channel 315, it will eventually flow past these stop junctions 115, allowing them to be wetted through from the side of the collection channel 315, thus eliminating the air-liquid barrier and causing the capillary forces preventing the liquid from moving forward to disappear.

This is actually a microchannel version of what happens when a filter is used, except, rather than just a few additional microchannels and capillary stop junctions, there are many thousands of very small microchannels and associated stop junctions, depending on the nature and size of the filter.

In FIG. 11, ideally, the liquid in the successive microchannels will already be at the stop junctions 115 before liquid in the collection channel 315 flows past them, otherwise bubbles may be trapped and further flow through the microchannels 111 will be blocked. Any number of microchannels 111 may be present depending on the needs of the application. The initial microchannel 110 can stem from the same source as the other microchannels 111, such as by branching off of them, or the liquid could come from an independent source.

Although it has been emphasized that filter- or membrane-based filtration has several advantages over microchannel filtration, the design illustrated in FIG. 11 can help reduce some of the limitations of microchannel filtration, or microfluidics in general where the need for successively smaller microchannels, either for size-exclusion filtering or to drive capillary flow, may be needed. In this design, the high capillarity present in the small microchannels 110 and 111 can be re-set to a less stringent system, which may be easier and more economical to fabricate.

Referring back to FIGS. 3A and 3B, which represent a basic structure where soluble matrix 200 is held between a filter 100 and a base material 310, liquid placed on or held against the filter 100 is drawn into the soluble matrix 200 and spans the distance or space 410 between the filter 100 and base material 310. At this point, the soluble matrix 100 dissolves, either completely or partially, but enough to release the filtrate from being held within it. However, the filtrate maintains its contact between the filter 100 and base material 310 in the form of a meniscus 400, which then spreads across the bottom surface of the filter 100 and wets through the filter 100 from the downstream surface, or the side of the filter 100 within the space 410, completing the process of initiating flow through the filter.

While the capillary force equations shown above have been used to compare capillary stop junctions with breakthrough pressure or bubble point, they have not yet been used to describe the movement and flow of fluid between the base material and filter. This is due to the complexity of the flow system, resulting from the fact that the filter is both porous and supplying liquid, or filtrate, to the advancement of the liquid spread. It has, however, been observed that the degree of hydrophilicity of the base material contributes to the rate of spread, so capillary forces still apply.

Figure 12:
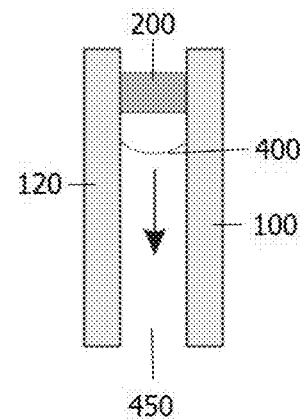
FIG. 12 illustrates a configuration of two filters with soluble matrix placed between them, and filtrate collected in the space between them, according to an embodiment.

FIG. 12 complicates modeling further by replacing the base material 310 of FIGS. 3A and 3B with another liquid-supplying filter 120, with filtrate collected in the space 450 between the two filters 100 and 120. With this structural modification, in the capillary force equations, the cosine term completely breaks down and must be replaced with a more complex variable. The remaining terms are sigma (σ), or surface tension of the liquid, and r, a function of the distance between the filters 100 and 120 spanning the space 450. Our goal is to maximize the volume of filtrate that is collected, so r is maximized. The remaining term is surface tension. While all capillary-driven systems are surface-tension-driven systems to some degree, the emphasis is usually on the hydrophilicity, or contact angle, of the materials involved. In our case, where contact angle, or its equivalent, is poorly defined, we fall back to the notion of surface tension as being a driving force of liquid spread between the filters 100 and 120, which correlates directly to the driving force of the filtration process.

Figure 13:
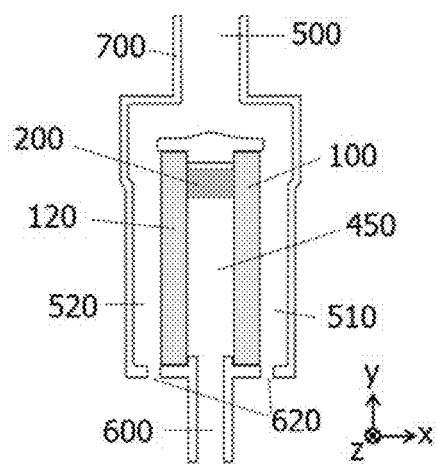
FIG. 13 illustrates a dual-filter separation device where filtrate is collected between the two filters, according to an embodiment.

Separation at the Point of Collection. FIG. 13 shows a device including the structure of FIG. 12 in a functional housing 700, where a common inlet 500 is divided into two sample chambers 510 and 520, to supply both filters 100 and 120 with an incoming sample, and where the filtrate that is collected between them in space 450 is extracted through an outlet 600. Not shown is a vent that would be used to facilitate filtrate extraction, where air replaces the filtrate that is drawn out the outlet 600. In addition, vents (e.g., at point 620) may be used to allow the input sample to flow into sample chambers 510 and 520, unless a vacuum source is used to facilitate the filling process. While a vacuum source could be used to facilitate filling of the chambers 510 and 520, it should not be used to initiate or support passage of filtrate through filters 100 and 120, as this would lead to hemolysis in the case of a blood sample.

In the case illustrated in FIGS. 12 and 13, as both filters 100 and 120 are saturated with the liquid sample, filtrate is drawn into the soluble matrix 200, this time from both sides. A meniscus 400 is formed between the two filters spanning the space 450 (herein also "filtrate chamber"), and as the filtrate is released from the soluble matrix 200 by its dissolution, the meniscus 400 and liquid spread across the bottom of both filters 100 and 120 to eventually fill the filtrate chamber 450. The filtrate is then drawn out of the filtrate chamber 450 by capillary forces generated by some downstream microfluidic system, or by positive pressure applied at the point of where a vent would normally be such as upstream of the soluble matrix 200, or by vacuum suction such as what may be supplied by an evacuated collection tube at the housing outlet 600, or by an electrowetting process.

The filters 100 and 120 used in FIGS. 12 and 13 do not necessarily need to be made of the same material, or, if including the same material, may be modified by various chemical or physical treatments different from one another. It is important, however, that flow rates through both filters 100, 120 allow the spread of the meniscus 400 between them in a fashion that allows the flow and filtration process to proceed.

Treatment of filters, or papers such as used in lateral flow immunological or molecular assays, and other surfaces that a sample may flow through or by or otherwise encounter in a system, is very common in diagnostic testing or sample processing applications, and various treatment methods and are well known in the art. Filters, papers, or surfaces can be treated with bovine serum albumin (BSA), casein, gelatin, or other reagents to block binding sites on the material to prevent or reduce non-specific binding of target biomolecules that flow through the system. Other reagents, such as salts, can alter surface charges or pH to reduce charge-based non-specific binding effects. Detergents or surfactants, such as Tween®, can be added to the structure of the filtration and sample processing system, to modify target biomolecules so that they do not stick to surfaces they encounter.

Many commercially available filters or membranes come pre-treated by the manufacturer to enhance wettability or, in the case of plasma separation membranes, reduce hemolysis. These treatments are often proprietary to the manufacturer. Although all of these filters are designed for a similar purpose (such as separating cells from plasma), the effect of these various treatments leads to different performance of the filter with regard to filtration efficiency for specific target biomarkers, or set of biomarkers. An optimization process is often used that involves selecting the most suitable filter for a specific biomarker or set of biomarkers, and additional treatments to be applied to that filter may be optimized to improve targeted specificity even further. This may be useful when designing a product for the specific application of the recovery of antibodies, antigens or nucleic acids, such as for detecting exposure to a coronavirus such as, e.g., SARS-CoV-2, or HIV, or other infectious diseases. A similar process of optimization and treatment may be performed for the recovery of nucleic acids, exosomes, or other valuable targets in the filtrate of the processed sample. In another application, a filter, or set of filters can be employed that ensure high recovery of antibody, but blockage of its corresponding antigen, to ensure the collected filtrate is not potentially hazardous.

Figure 14:
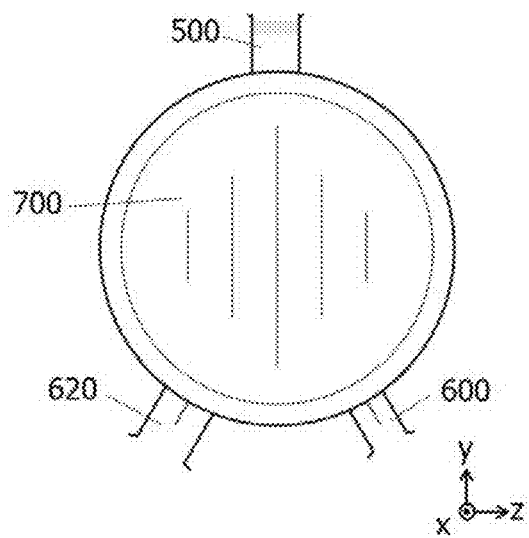
FIG. 14 illustrates an external cartridge configuration of the dual-filter separation device of FIG. 13 with its associated input and output fittings, according to an embodiment.

FIG. 14 illustrates a specific housing design 700 for the dual filter system, or a filtration cartridge, where the use is for plasma extraction from input whole blood. The circular nature of the cartridge 700 is just for illustration, as the shape of the cartridge could also be square or rectangular. FIG. 13 can be considered a cross-sectional view of FIG. 14, with coordinate systems shown to the bottom right of the illustrations for the purpose of clarifying the orientation of the diagrams. The inlet 500 of the filtration cartridge 700 is intended to be inserted in a shielded venous access port or venous line, where a needle is inserted into a vein, usually in the arm, as is common practice in phlebotomy. The housing or cartridge 700 may be evacuated itself to facilitate drawing blood into the cartridge 700 through the venous access point; alternatively, an evacuated tube, or vacu-tube, similar to what are commonly used in phlebotomy, may be attached to the filtration cartridge at the opposite end of the cartridge with a fitting that is similar to the shielded access point where the filtration cartridge 700 is inserted to draw blood. The vacuum suction force of the vacu-tube loads sample into chambers 510 and 520 of FIG. 13. The sample may also continue to be drawn into the vacu-tube, if desired, or the vacu-tube may be removed after the cartridge 700 is filled. Alternatively, a syringe can be attached at point 620 to draw blood into the cartridge 700, or the pressure of the blood flow from the access point connected at the inlet 500 may be sufficient to fill the cartridge 700. In this configuration, the connector would be replaced with a vent to allow filling. Once filled, the cartridge 700 itself may be removed from the blood source and set aside while plasma passes through the filters and fills the filtrate chamber.

When the filtrate chamber is filled, a vacu-tube is connected to the filtration cartridge 700 at the point of the connection for filtrate removal (outlet 600) where the filtrate is drawn out by vacuum force of the vacu-tube. Alternatively, the outlet or filtrate removal fitting could be replaced with a luer fitting to connect a syringe to draw filtrate out, or some other appropriate design.

The benefits of immediate plasma separation at the point of blood collection are numerous. Many sensitive or delicate biomarkers, or indicators of a disease state or condition, rapidly degrade in the presence of cells once removed from the body, where they are no longer replenished by the disease source or condition within the body that produced them. These biomarkers are usually degraded by cell membrane surface receptors. Separating cells from the plasma immediately helps preserve these biomarkers for later study. While there are many additives used to preserve delicate biomarkers, these additives also often interfere with downstream analysis. This is why it is common that many centrifuge tubes are filled by a phlebotomist at the time blood is collected, rather than a single tube, because each tube has a different combination of preservatives and anticoagulants. It would be better to fill just one tube, extract the plasma immediately, and not use potentially interfering preservatives and reagents. Plasma, in the absence of cells, can also be frozen for preservation, whereas to freeze whole blood results in considerable hemolysis which may generate interference in downstream analysis.

The method and structure described in this disclosure could be used to separate small volumes of plasma from a small volume of blood, which may be desirable in case the individual from whom the blood is collected is ill or young and large volumes are not available for collection. The dual filter design of this disclosure can also lead to the processing of larger blood volumes, including in the milliliter range, due to the increased surface area available with two filters rather than one. Rapid separation of plasma from whole blood is beneficial because the plasma can be used immediately in a diagnostic test. If not tested immediately, the plasma can be sent to a lab for analysis. Sending plasma to a lab for testing has the additional benefit of minimizing the chance of error by minimizing hands-on intervention and reducing the workflow of laboratory technicians who normally must further process the blood later, including by centrifuging the sample. A sample can be collected and processed remotely, such as in the field or at home, with purified liquid plasma being delivered to a lab. While this eliminates the need to centrifuge the sample once it arrives at the lab, it also is far simpler than other remote sample collection methods that often depend on drying a sample out on a card or on beads. The sample reconstitution methods required by these platforms are very complicated and time consuming.

Sample Fractionation, Enrichment. Collection and Analysis. The device of FIGS. 13 and 14 can be useful for not just rapid plasma separation at the point of blood collection, but for additional sample processing steps leading to ultimate diagnostic analysis. Beads with functionalized surfaces used to capture, concentrate or label components of blood fractions can be placed in sample chambers 510, 520 and/or in the filtrate collection chamber 450 of FIG. 13, to interact with the blood fractions before, during, or after plasma separation. These beads can be removed later once the separation process is complete.

Figure 15:
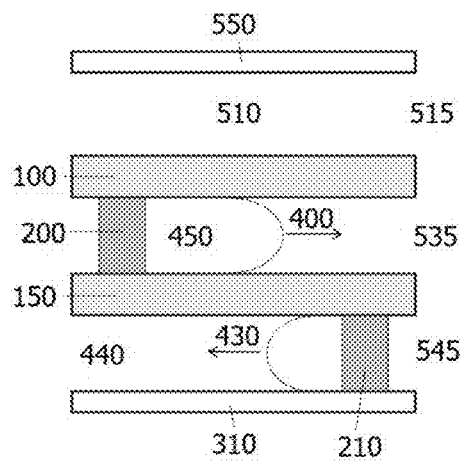
FIG. 15 illustrates another dual-filter separation device, where an inlet sample is separated into three filtrate fractions that can be removed for further analysis, according to an embodiment.
Figure 16:
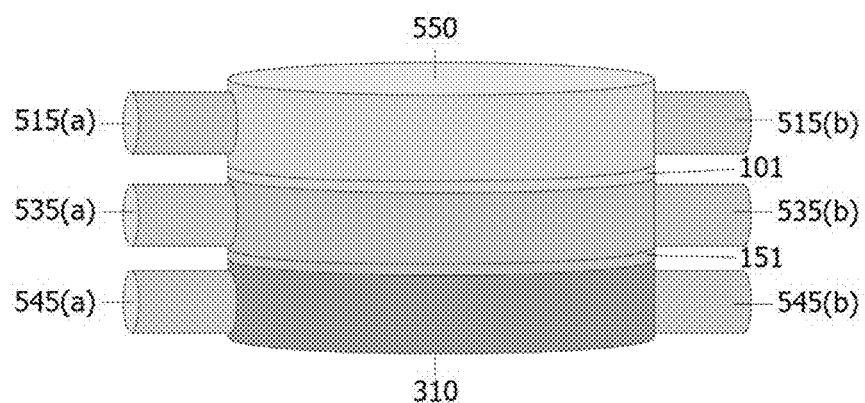
FIG. 16 illustrates an external cartridge housing for the dual-filter, three-fraction device of FIG. 15, with various inlets and outlets, according to an embodiment.

FIG. 15 illustrates a device where the inlet sample is separated into three fractions, each of which can be extracted for further analysis. FIG. 16 is one possible external cartridge design to accompany FIG. 15. Referring to FIG. 15, the first fraction is the residue or retentate left in the sample inlet chamber after the filtration is completed. Each chamber or space can be connected to inlets, outlets and vents, as may be needed, for washing out the contents of the space for further analysis. While these components are not shown in FIG. 15, where they are anticipated in the areas labeled as 515 for the first fraction, 535 for the second fraction and 545 for the third fraction, they are listed in FIG. 16 and labeled 515(a) and 515(b) for the inlet and outlet, respectively, for the first fraction, 535(a) and 535(b) for the second fraction and 545(a) and 545(b) for the third fraction. Each space 510, 450 and 440 may contain beads or other reagents to facilitate capture, collection, enrichment and/or concentration of specific analytes or biomarkers. Extraction or elution of a fraction of interest may be performed by washing out the space where the fraction is located. It may also be extracted by washing through the filters 100 or 150 from the fraction space below, or back-flushing the filter and collecting the back-flushed liquid.

In FIG. 15 the first soluble matrix 200 eliminates the breakthrough pressure requirement of filter 100. The resulting filtrate passes into the space above filter 150 and is drawn through filter 150 by the use of the second soluble matrix 210. The remaining material above filter 150 is the second fraction, which is washed out via the valves and ports in the general area indicated by 535. The second filtrate material becomes the third fraction, and is washed out or recovered via 545. The base of the device is labeled 310. The filtrate of filter 100 that is drawn through by soluble matrix 200 spans the gap between the two filters 100 and 150, and forms a meniscus 400 that spreads across both filters. Once it reaches the second soluble matrix 210, the second filtrate is drawn through filter 150 and spans the gap between filter 150 and base 310, with the meniscus 430 spreading back across the remaining bottom surface of filter 150. Soluble matrix 210 must be placed at the furthest point away from soluble matrix 200 to ensure that the largest possible bottom surface area of filter 100 is recruited to engage in filtration, and to ensure that the top of filter 150 is also completely saturated with filtrate before breakthrough is initiated in filter 150 by the second soluble matrix 210. This placement of soluble matrix 210 could be at the geometrically furthest point from soluble matrix 200, or it could be the furthest point from the flow of filtrate between the two filters 100 and 150, which is not necessarily the same as the furthest point geometrically due to the possible presence of flow control structures and filter support structures not shown in FIG. 15. The correct placement of the soluble matrices 200 and 210 are best determined empirically.

In the external housing design illustrated in FIG. 16, the various inlets and outlets may have valves connected to them to control the washing and elution steps that may take place to recover the biomarkers or fractions of interest. For example, to recover the second fraction, in the area of 450 of FIG. 15, filter 150 may be washed by passing elution buffer through the inlet 535(a) and out the outlet 535(b), or filter 150 may be back-flushed by passing elution buffer through inlet 545(a) and out 535(b). Alternatively, the device of FIG. 16 can be disassembled and filter housing 151 could be removed for analysis of the composition on top of filter 150. The same methods could be used for analyzing the first fraction above filter 100, or filter housing 101.

In another configuration of FIG. 16, the cover 550 could be open and the sample can be added from above rather than through the inlet 515(a). The benefit of the device illustrated in FIGS. 15 and 16 is that it allows to perform multi-component fractionation without the need for centrifugation or vacuum, which may damage components of a fraction and/or embed important components of a fraction in the filters that are used, making them more difficult to recover. The same concepts can be used for fractionation systems that have more than two filters, and whether the filters or cartridge design is circular, cylindrical or rectangular or any other shape is not relevant for the purposes of demonstration of the principles of the technology disclosed in the present application and how it can be employed for this purpose.

Tubular or Cylindrical Filters. FIGS. 17 and 18 can be considered three-dimensional configurations of the planar geometries illustrated in FIGS. 3 and 12. Under normal circumstances, the structure in FIG. 17 is rarely used because pressure would need to be applied to force the inlet sample liquid 517 through the filter 107 and into the filtrate collection area 417, which is within the center lumen of the tube. Any such applied pressure would likely collapse the filter 107 due to a build-up in pressure within the housing of the device 707. In the case where soluble matrix 207 is placed within the center lumen, no collapse would take place because no pressure is applied, and filtrate fills the collection area 417 along the flow path 452, initially at the point of the soluble matrix 207, and then along the entire length of the filter 107 as a meniscus that forms within the central lumen spreads. After the filtrate collection area 417 is full, the filtrate can be easily extracted from within the central lumen of the filter 107.

FIG. 18 is a more common method of filtration where pressure is applied to the sample inlet stream 518 inside the lumen of the tube filter 107, and filtrate collects in the space 418 outside, between the filter 107 and the device housing 707. However, in the case where soluble matrix 208 is used, no pressure needs to be applied to initiate filtration, and filtrate passes through the filter 1080 in the direction of 452. A meniscus spreads between the filter 107 and the outer housing 707, starting at the point of the soluble matrix 208, and extending along the entire length of filter 107.

The benefit of the designs illustrated in FIGS. 17 and 18 is the potential for an increase in surface area for filtration within a small, compact design. This is especially important in plasma separation methods where filters are specified in microliters (μL) of whole blood per square centimeter ($cm^2$) surface area of the filter. Blood cannot be continuously filtered through plasma separation filters because the filter's pores clog with cells. Increasing the available surface area within a given space is helpful in preventing the entire device design from becoming too large. It is possible that multiple tubular filters could be used simultaneously, and it is possible tubular filters have more likelihood of fitting within a centrifuge tube or test-tube style platform, as is often used in laboratory sample collection and analysis. The single tube and housing structure could also be wound spirally to further facilitate an increased surface area for a given available fixed space.

Similar to FIG. 1S, one tubular filter could be placed inside another tubular filter, with soluble matrix between them, to accommodate multiple fraction separation and processing.

FIGS. 19A and 19B illustrate another embodiment of the concept of FIG. 18. In this case, the filter 109 is closed at one end and the majority of filtrate 401 collects on the bottom portion 460 of the tube 709, and the tube base is changed to a stoppered outlet or septum 710. When the liquid sample is added to the center lumen 519 of the filter 109, filtrate 401 passes through the filter 109 and to the space 419 between the filter 109 and the tube wall 709. As it flows it collects or pools in the bottom portion of the tube 460. The central lumen can be refilled with sample continuously until the outer space and pooling area 460 is filled, or if the filter 109 becomes clogged, until no more filtrate passes through the filter. At this time the inlet could be stoppered, and the tube 709 can be inverted so that the filtrate 401 can be accessed, such as in an automated system, by puncturing through the stopper or septum 710 to retrieve the filtrate via aspiration.

The concepts described above and illustrated in FIG. 17-19B could also be modified to work with multiple tubular filters in a single external tube structure, or with a filter folded into a reticulated or serpentine circular fashion to maximize the surface area of filter within a given space. Instead of tubular filters, planar filters rolled and welded into a tube shape, or rectangular or square or other useful geometry can also be employed.

Figure 20:
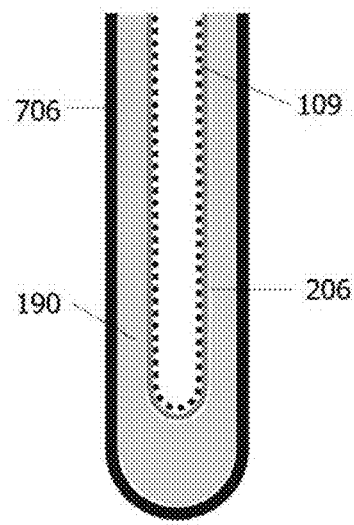
FIG. 20 illustrates a method of concentrating particulate components of a sample by allowing aqueous components to flow out of a sample and into a surrounding absorbing material, the initiation of which flow is facilitated by the use of soluble matrix, according to an embodiment.

Particulate Concentration. FIG. 20 illustrates a convenient design where a tubular filter 100, closed at one end, is inserted into a tube-like structure 706 with soluble matrix 206 and absorbing material 190 filling the space between the filter 106 and tube wall 706. In this design, the sample of interest, such as blood or urine, is loaded into the inner filter. Excess liquid passes out of the filter 106, assisted by the soluble matrix 206, and into the absorbing material 190 that functions like a suction pump to continue to draw liquid out of the filter inner lumen. Suitable adsorbing material includes cellulose, which is commonly used as an absorbing material at the downstream end of a lateral flow test strip, or glass fibers. In this case, when the filtrate is not recovered, there is no need to minimize the soluble matrix 206, which can enclose the entire outside surface of the filter 106, to facilitate transfer between the filter and the absorbing material 190. While it is possible that filtrate could flow directly from the filter 106 to the absorbing material 190, if they are in physical contact with each other, in practice, due to imperfections in geometry or spaces caused by a filter structural support layer, the flow is not efficient and would be improved by the presence and facilitation of the soluble matrix layer 206. Also, if the capillarity of the filter 106 is higher than that of the absorbing material 190, flow into 190 will not proceed efficiently. In this situation, soluble matrix 206 would be necessary to initiate flow through the filter 106 into 190.

Sample can continue to be loaded into the inner filter structure as its level drops, due to the passage of liquid through the filter 106 and into the absorbing layer 190. This residue will become increasingly thick within the inner filter lumen and can, eventually, be washed out and recovered for analysis.

The sequential layers of filter 106, soluble matrix 206, and absorbing material 190 are useful to remove excess liquid from a sample, also called negative enrichment. This sequence, as shown in FIG. 20, can also be used in a planar fashion, or other geometrical shape as may be useful.

Figure 21:
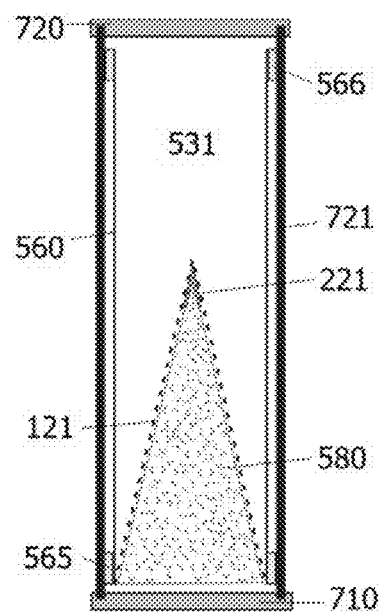
FIG. 21 illustrates a cone-shaped separation system in a tube geometry where filtrate passes from an inlet side to an outlet side, the collection of filtrate aided by a sponge or foam member located within or on the downstream side of the cone, according to an embodiment.

Inverted Cone Filter. Another geometry that has beneficial properties for separating and collecting a filtrate through a filter is the inverted cone design illustrated in FIG. 21. Instead of the absorbing material 190 from FIG. 20, from which the filtrate is not intended to be retrieved, FIG. 21 shows a sponge or foam structure 580 used to facilitate filtrate collection, but also accommodate filtrate retrieval by removal of the sponge or foam 580 from the structure 721, or compression of the sponge or foam while within the structure 721, pushing the collected filtrate out and causing it to pool in a manner that facilitates retrieval. The cone shape allows for a simple means of increasing the surface area of filtration within a limited and confined space, but without the need of complex fittings or connectors as may be needed for a spiral-wound system or multi-cylinder systems.

As has been described, it is important for a meniscus to form between the filter and some additional structure to facilitate spread of the filtrate across the whole bottom surface area of the filter, in order to recruit the entire filter for filtration. This is accomplished by the sponge or foam 580 being in close proximity to the downstream surface of the filter 121 and the meniscus connecting and spreading between the downstream surface of the filter 121 and the upper surface of the foam or sponge 580. The soluble matrix 221 could be at the apex of the cone (as shown) or base of the cone (not illustrated), depending on the needs of the system.

It is anticipated that the filtration would take place within an enclosed geometry. As such, a negative pressure could develop within the sample side 351 of the structure, or upstream area of the cone 121, and the filtrate or sponge side of the cone 580, which would reduce filtration rate over time. This is because the entire device would be sealed from the outside environment due to septums or caps 720, 710 on the sample side and the filtrate side. To prevent this build-up of negative pressure, a method of pressure equalization is needed to recirculate displaced air from the sponge area 580 back into the upstream sample area 531, to accommodate passage of filtrate from the upstream area into the sponge area. This could be accomplished by an inner-wall 560 and outer-wall 721 geometry with hydrophobic filter vents 565 and 566 separating the two and allowing passage of air but not sample or filtrate. This is illustrated in FIG. 21 and represents one among several possible methods of equalizing pressure. A hydrophobic or hydrophobically coated hole between the two sides may also be sufficient for pressure equalization rather than filter vents (not shown).

A frame, not shown, could be used to support the filter 121 and would be placed on the upstream surface of the filter to prevent filter deformation due to the weight of the sample. Also, a means for extracting filtrate from the structure 721 could be to invert the device so the cone opening is facing upward, and a needle or pipette could pass through the septum 710, or the septum 710 could be removed, and the tip of the needle or pipette could depress the foam or sponge 580 surface causing displacement of the filtrate out of the foam or sponge and allowing the filtrate to pool on the foam or sponge surface, where it could be retrieved. The frame mentioned would also provide mechanical strength to the filter so the pressure of the needle or pipette tip on the foam or sponge would not cause it to rupture or push-through the filter.

Microplate Filtration. Microplates are commonly used in automated, semi-automated, or high-throughput sample processing and analysis. In many cases beads are used to facilitate sample processing. Filtration microplates have been developed to facilitate multiple sample processing steps including sample loading, analyte capture, washing and multiple reagent delivery steps, with beads remaining in the wells of the microplate during the entire process. The excess liquids are removed by suction or centrifugation through the microplate well bottom, which is made of a filter.

FIG. 22A illustrates a typical filtration microplate design 800 which makes use of a centrifuge or vacuum pump in the area of 900, and FIG. 22B illustrates a design which makes use of a new design 850 using a soluble matrix 200. As described for FIG. 20, the soluble matrix 200 helps bridge the gap between the filter 100 and the absorbing material 190. In the case of the new design 850, the microplate can remain on the soluble matrix 200 and absorbing material pad 190 during washing and reagent delivery steps, with the excess liquid slowly draining out of the well through the filter 100 during the various liquid delivery steps. The microplate 850 could also be removed from the pad and left on a holder suspending the bottoms of the microplate wells, where the filters 100 are in the air so no or very little liquid seeps out.

An advantage of the filtration microplate method using a soluble matrix is a simplification in microplate design, such as no need for the filter support 810 and no need for additional equipment 900 to perform the liquid removal steps, and no need for repeated cleaning and maintenance of equipment that is no longer being used. The use of the soluble matrix 200 can insure or improve the consistency of filtration between wells in case the vacuum, or centrifugation, was not applied evenly on each well. It will also prevent lysis of cells and enable analysis of cells and plasma separately in case the plasma is collected and analyzed in a separate plate.

Although the inventive subject matter has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

What is claimed is:

1. A device for extracting a filtrate from a liquid sample, the device comprising:
   at least one filtration membrane; and
   a soluble matrix in physical contact with at least a portion of a downstream surface of the at least one filtration membrane, the soluble matrix possessing a capillary drawing force sufficient to draw filtrate through the at least one filtration membrane and into the soluble matrix, causing the soluble matrix to at least partially dissolve or disintegrate in the filtrate, whereby the filtrate is released.

2. The device of claim 1, further comprising a base material, support membrane, or housing to hold the soluble matrix in contact with the at least one filtration membrane.

3. The device of claim 1, wherein the at least one filtration membrane is a plasma separation membrane.

4. The device of claim 1, wherein the at least one filtration membrane comprises two filtration membranes arranged substantially in parallel at a separation distance from each other and facing each other with their downstream surfaces, the soluble matrix being held between the downstream surfaces of the two filtration membranes and spanning the separation distance, the separation distance between the two filtration membranes being sufficiently small to cause the filtrate to wick along the downstream surfaces of the two filtration membranes upon at least partial dissolution or disintegration of the soluble matrix.

5. The device of claim 4, wherein the plasma separation membrane is treated to improve filtering performance for a specified biomarker.

6. The device of claim 5, wherein the specified biomarker is an antibody, antigen or nucleic acid component of or for a coronavirus.

7. The device of claim 4, further comprising a housing containing the two filtration membranes and the soluble matrix therebetween and defining an inlet in fluid communication with upstream surfaces of the two filtration membranes and an outlet in fluid communication with downstream surfaces of the two filtration membranes and with the soluble matrix.

8. The device of claim 1,
   wherein the at least one filtration membrane is a first filtration membrane and the soluble matrix is a first soluble matrix,
   wherein the device further comprises one or more downstream filtration membranes each having in physical contact with its downstream surface, an associated downstream soluble matrix possessing a capillary drawing force sufficient to draw filtrate through the filtration membrane, the one or more downstream filtration membranes and the one or more associated downstream soluble matrixes forming, together with the first filtration membrane and the first soluble matrix, an alternating sequence of filtration membranes and soluble matrixes,
   wherein each of the downstream soluble matrixes in the sequence extends across a respective gap between the downstream surface of the associated one of the filtration membranes by which it is preceded in the sequence and an upstream surface of a filtration membrane by which it is followed in the sequence or of a base member of the device, and possesses a capillary drawing force sufficient to draw filtrate through the preceding one of the filtration membranes and into the soluble matrix,
   the device further comprising a housing containing the alternating sequence of filtration membranes and soluble matrixes and defining an inlet in fluid communication with an upstream surface of the first filtration membrane and multiple outlets each in fluid communication with a downstream surface of one of the filtration membranes.

9. The device of claim 8, wherein filter properties of the filtration membranes differ along the sequence, whereby the liquid sample is fractionated into a retentate fraction, one or more filtered retentate fractions, and a final filtrate fraction.

10. The device of claim 8, wherein successive soluble matrixes in the sequence, one being in physical contact with an upstream surface of one of the downstream filtration membranes and another one being in physical contact with a downstream surface of that downstream filtration membrane, are spaced apart along that downstream filtration membrane.

11. The device of claim 8, wherein the alternating sequence of filtration membranes and soluble matrixes comprises multiple nested tubular filtration membranes and one or more soluble matrixes therebetween.

12. The device of claim 1, wherein the at least one filtration membrane comprises a tubular filtration membrane and the soluble matrix is placed inside the tubular filtration membrane in physical contact with an interior surface of the tubular filtration membrane, wherein an inner diameter of the tubular filtration membrane is sufficiently small to cause the filtrate to wick along the cylindrical filtration membrane in a longitudinal direction upon dissolution or disintegration of the soluble matrix.

13. The device of claim 12, further comprising a housing containing the tubular filtration membrane and the soluble matrix and defining an inlet in fluid communication with an exterior surface of the tubular filtration membrane and an outlet in fluid communication with a center lumen of the tubular filtration membrane and with the soluble matrix.

14. The device of claim 1, wherein the at least one filtration membrane comprises a tubular filtration membrane and the soluble matrix is placed at least partially surrounding the tubular filtration membrane in physical contact with an exterior surface of the tubular filtration membrane, the device further comprising a tubular housing containing the tubular filtration membrane and the soluble matrix and defining an inlet in fluid communication with a center lumen of the tubular filtration membrane and with the soluble matrix, wherein a separation distance between an interior surface of the tubular housing and the exterior surface of the tubular filtration membrane is sufficiently small to cause the filtrate to wick along the tubular filtration membrane in a longitudinal direction upon at least partial dissolution or disintegration of the soluble matrix.

15. The device of claim 14, wherein the tubular filtration membrane comprises a closed end.

16. The device of claim 14, wherein the housing further defines an outlet in fluid communication with an exterior surface of the tubular filtration membrane.

17. The device of claim 14, wherein the housing is closed on one end by a stoppered outlet.

18. The device of claim 1, wherein the at least one filtration membrane comprises a tubular filtration membrane and the soluble matrix lines an exterior surface of the tubular filtration membrane, the device further comprising a housing containing the lined tubular filtration membrane and a filtrate absorbing material filling a space between the soluble matrix of the lined tubular filtration membrane and the housing.

19. The device of claim 1, wherein the filtration membrane is conical in shape and supported by a conical sponge structure, and wherein the soluble matrix is placed between the conical sponge structure and the conical filtration membrane.

20. The device of claim 19, further comprising a tubular housing comprising a septum on which the conical sponge structure rests.

21. A device for extracting a filtrate from a liquid sample, the device comprising:
 a pair of filtration membranes facing each other with their downstream surfaces; and
 a soluble matrix held between and in physical contact with at least portions of the downstream surfaces of the pair of filtration membranes, the soluble matrix possessing a capillary drawing force sufficient to draw filtrate through the at least one filtration membrane and into the soluble matrix, causing the soluble matrix to at least partially dissolve or disintegrate in the filtrate, whereby the filtrate is released.

* * * * *